(12) United States Patent
Zastrozna

(10) Patent No.: US 11,751,926 B2
(45) Date of Patent: *Sep. 12, 2023

(54) ANGLED FLUTES IN CANNULATED BONE SCREWS

(71) Applicant: DePuy Synthes Products, Inc., Raynham, MA (US)

(72) Inventor: Anna Zastrozna, Teaneck, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/351,495

(22) Filed: Jun. 18, 2021

(65) Prior Publication Data

US 2021/0307800 A1   Oct. 7, 2021

Related U.S. Application Data

(63) Continuation of application No. 15/958,541, filed on Apr. 20, 2018, now Pat. No. 11,076,901.

(Continued)

(51) Int. Cl.
*A61B 17/86* (2006.01)

(52) U.S. Cl.
CPC .......... *A61B 17/863* (2013.01); *A61B 17/864* (2013.01); *A61B 17/8605* (2013.01); *A61B 17/8635* (2013.01)

(58) Field of Classification Search
CPC .............. A61B 17/863; A61B 17/8605; A61B 17/8635; A61B 17/864; F16B 25/106; F16B 25/103; F16B 25/00; F16B 25/0084

(Continued)

(56) References Cited

U.S. PATENT DOCUMENTS

| 2,847,885 A | 8/1958 | Wagner |
| 3,044,341 A | 7/1962 | Stern |

(Continued)

FOREIGN PATENT DOCUMENTS

| CA | 2736775 A1 | 3/2010 |
| CN | 101297767 A | 11/2008 |

(Continued)

OTHER PUBLICATIONS

Edge Orthopaedics Bite Compression Screws, http://edgeorthopaedics.com/bite-compression-screws, website accessed Apr. 17, 2016.

(Continued)

*Primary Examiner* — Jessica Weiss
(74) *Attorney, Agent, or Firm* — BakerHostetler

(57) ABSTRACT

A bone screw, comprising a proximal end and a distal end spaced from the proximal end in a distal direction along a longitudinal axis of the bone screw and a cannulation extending from the proximal end to the distal end. The bone screw further including a threaded region extending along at least a portion of a length of the screw, the length extending from the proximal end to the distal end. The threaded region defining at least one external thread that extends about the longitudinal axis along a helical path. The threaded region includes at least one flute that extends to the distal end of the bone screw. The at least one flute defines an associated at least one cutting tooth that, in turn, defines a cutting face oriented so as to define an angle with respect to the longitudinal axis. The angle is in the range of about 5 degrees and about 25 degrees, and the flute circumferentially interrupts at least a portion of the external thread.

19 Claims, 19 Drawing Sheets

Related U.S. Application Data

(60) Provisional application No. 62/488,398, filed on Apr. 21, 2017.

(58) Field of Classification Search
USPC .......................... 606/300–321; 411/412–413, 411/387.1–387.8, 386
See application file for complete search history.

(56) References Cited

U.S. PATENT DOCUMENTS

| | | | |
|---|---|---|---|
| 3,130,763 A * | 4/1964 | Schlosser | B23B 51/04 |
| | | | 408/205 |
| 3,738,218 A | 6/1973 | Gutshall | |
| 3,866,509 A | 2/1975 | Kraus et al. | |
| 4,212,568 A | 7/1980 | Minicozzi | |
| 4,414,966 A | 11/1983 | Stednitz | |
| 4,537,185 A * | 8/1985 | Stednitz | A61B 17/8635 |
| | | | 606/304 |
| 5,098,435 A * | 3/1992 | Stednitz | A61B 17/1637 |
| | | | 606/907 |
| 5,120,172 A | 6/1992 | Wakai | |
| 5,129,901 A | 7/1992 | Decoste | |
| 5,334,204 A * | 8/1994 | Clewett | A61B 17/8625 |
| | | | 606/312 |
| 5,897,319 A | 4/1999 | Wagner et al. | |
| 6,306,140 B1 * | 10/2001 | Siddiqui | A61B 17/863 |
| | | | 606/315 |
| 6,402,757 B1 | 6/2002 | Moore et al. | |
| 7,037,309 B2 | 5/2006 | Weil et al. | |
| 7,582,107 B2 | 9/2009 | Trail et al. | |
| 7,708,738 B2 | 5/2010 | Fourcault et al. | |
| 7,731,738 B2 * | 6/2010 | Jackson | A61B 17/8635 |
| | | | 606/305 |
| 8,267,977 B2 | 9/2012 | Roth | |
| 8,511,958 B2 | 8/2013 | Chang | |
| 8,647,038 B2 | 2/2014 | Gong et al. | |
| 2002/0127085 A1 | 9/2002 | Field | |
| 2003/0028193 A1 | 2/2003 | Weil et al. | |
| 2007/0025827 A1 | 2/2007 | Pryor | |
| 2007/0162028 A1 * | 7/2007 | Jackson | A61B 17/8635 |
| | | | 606/86 A |
| 2007/0269288 A1 | 11/2007 | Palm | |
| 2011/0318137 A1 | 12/2011 | Chen | |
| 2013/0158610 A1 | 6/2013 | Hernandez | |
| 2014/0257409 A1 * | 9/2014 | Reed | A61B 17/8625 |
| | | | 606/304 |
| 2014/0277188 A1 | 9/2014 | Poulos | |
| 2015/0134014 A1 | 5/2015 | Palmer et al. | |
| 2016/0120583 A1 * | 5/2016 | Bales | A61B 17/8625 |
| | | | 606/311 |
| 2016/0310187 A1 | 10/2016 | Leibinger et al. | |
| 2020/0337811 A1 | 10/2020 | Fromovich | |

FOREIGN PATENT DOCUMENTS

| | | |
|---|---|---|
| CN | 102058426 A | 5/2011 |
| CN | 103156679 A | 6/2013 |
| CN | 106037917 A | 10/2016 |
| CN | 106456289 A | 2/2017 |
| EP | 0425358 A1 | 5/1991 |
| FR | 2840799 A1 | 12/2003 |
| FR | 3000664 A3 | 7/2014 |
| JP | 2788078 B2 | 8/1998 |
| JP | 2003-024343 A | 1/2003 |
| JP | 2004-033767 A | 2/2004 |
| JP | 2016-536074 A | 11/2016 |
| WO | 2009/130415 A2 | 10/2009 |
| WO | 2014/056017 | 4/2014 |

OTHER PUBLICATIONS

Medartis SpeedTip CCS, Product Information, http://www.medartis.com/products/aptus/foot/speedtip-ccs-22-30-cannulated-compression-screws, website accessed Jun. 15, 2016.

Trilliant Surgical Tiger Screws, http://trilliantsurgical.com/products/tiger-headless-cannulated-screw-system, website accessed May 30, 2016.

Wright Medical OrthoPro CSS http://www.wright.com/footandankleproducts/css-cannulated-screw-system, website accessed May 30, 2016.

* cited by examiner

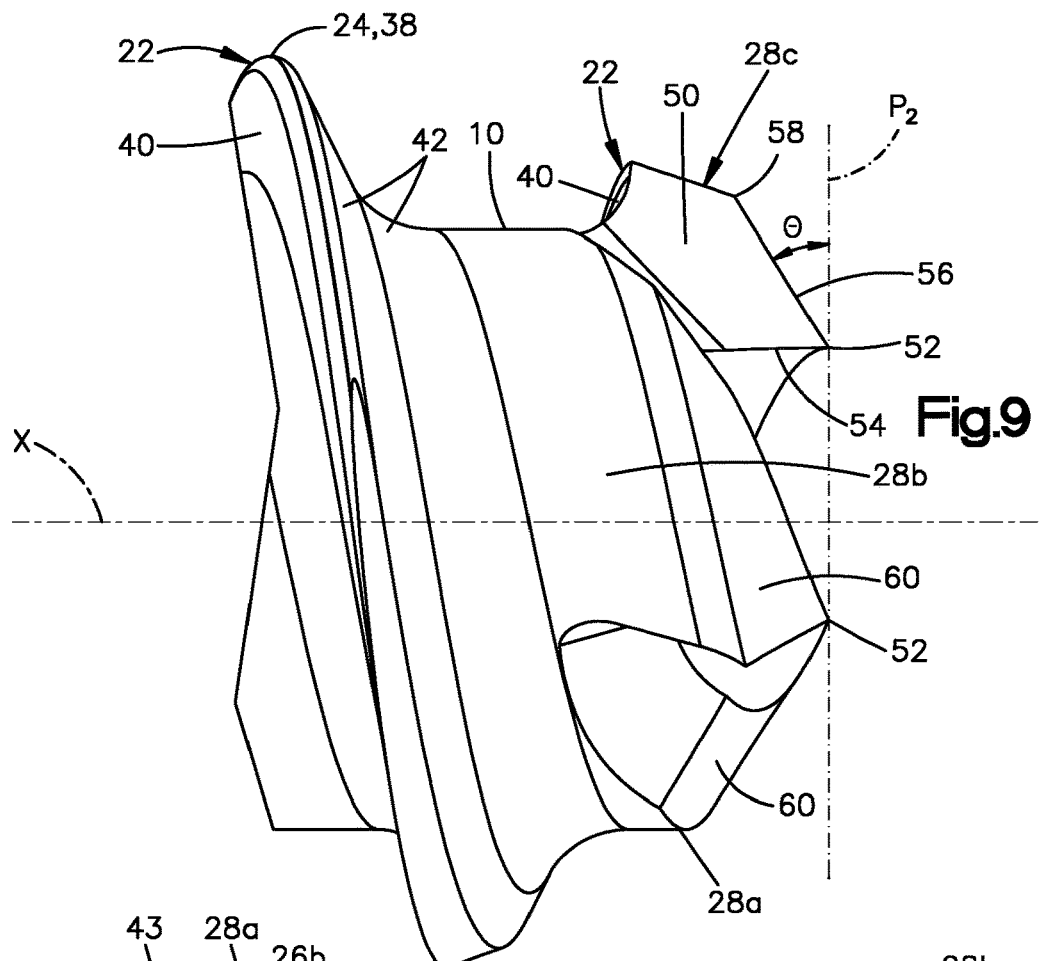
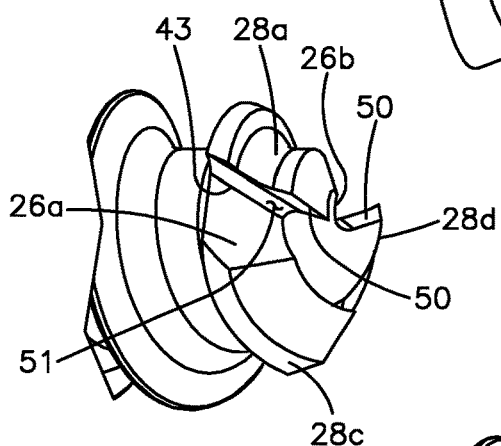
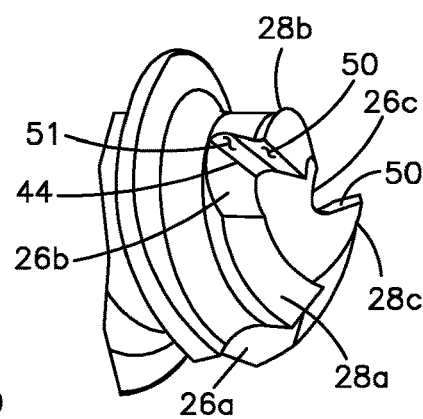
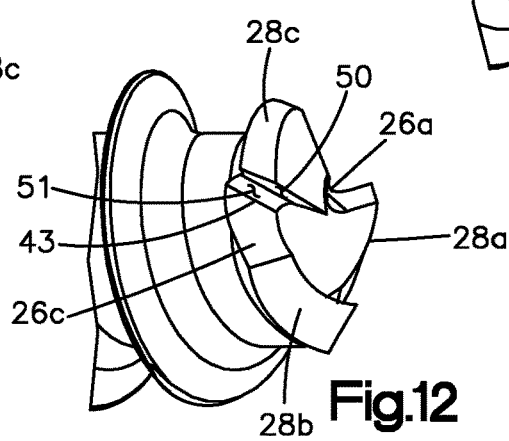
Fig.9
Fig.10
Fig.11
Fig.12

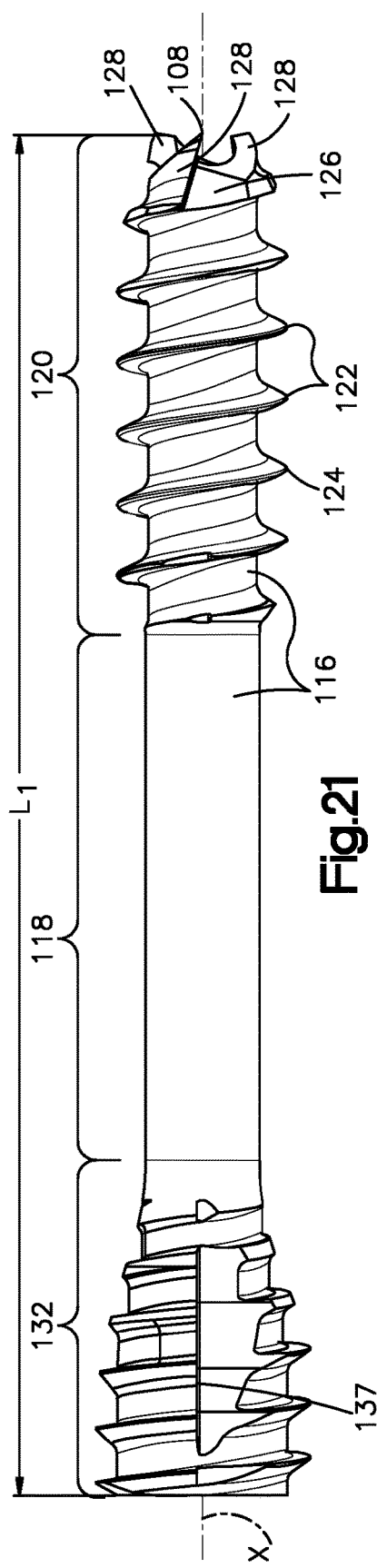
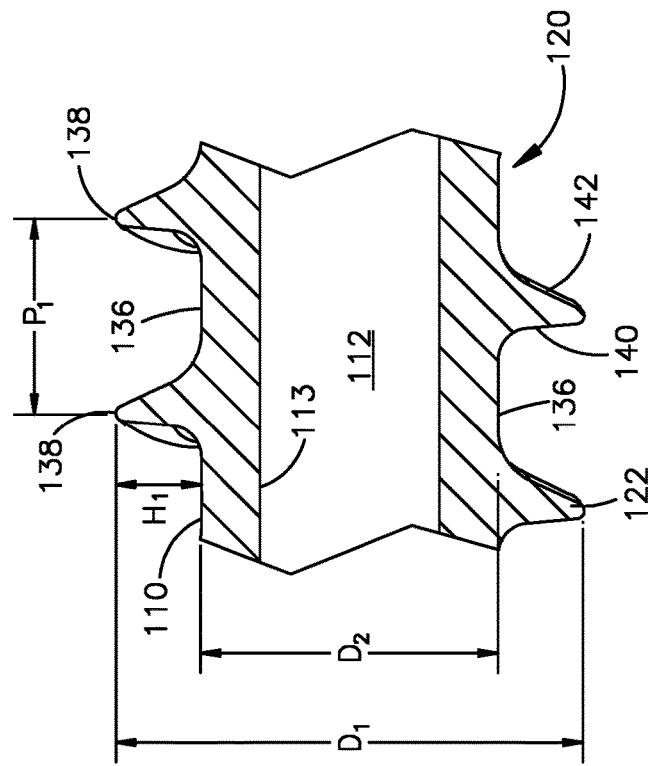
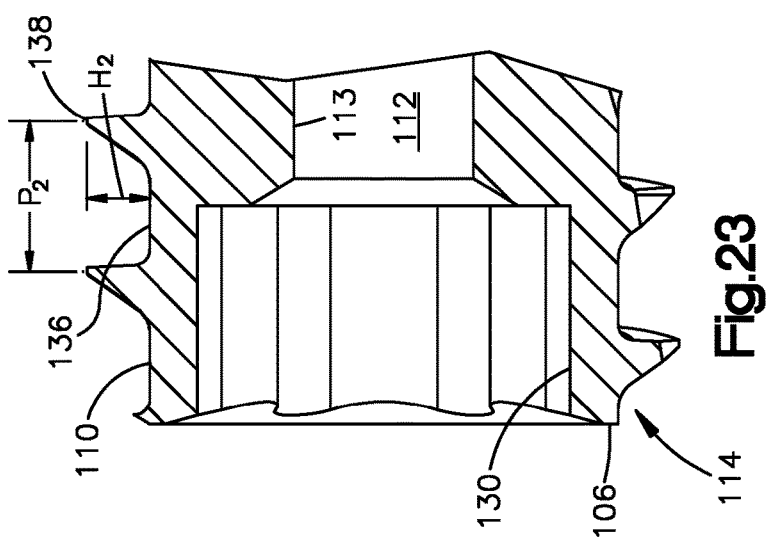

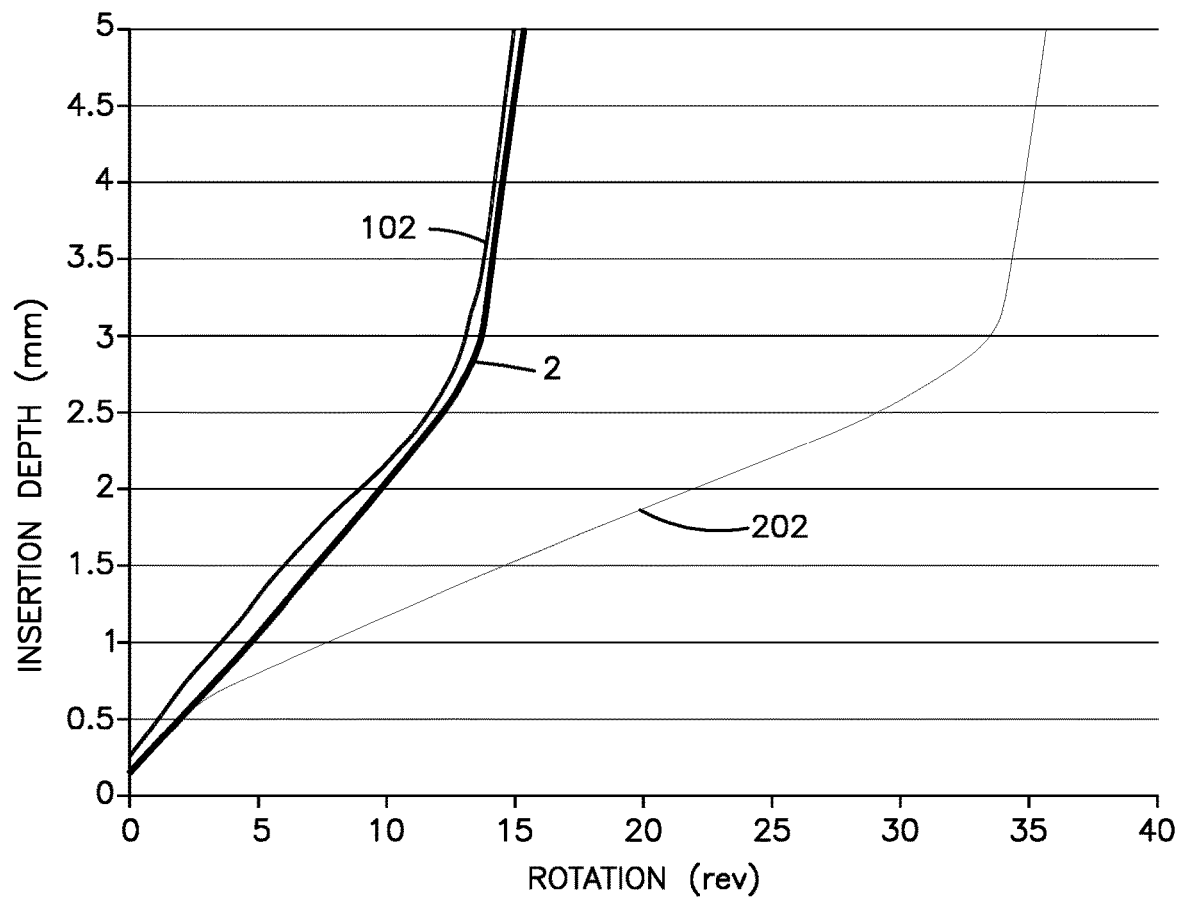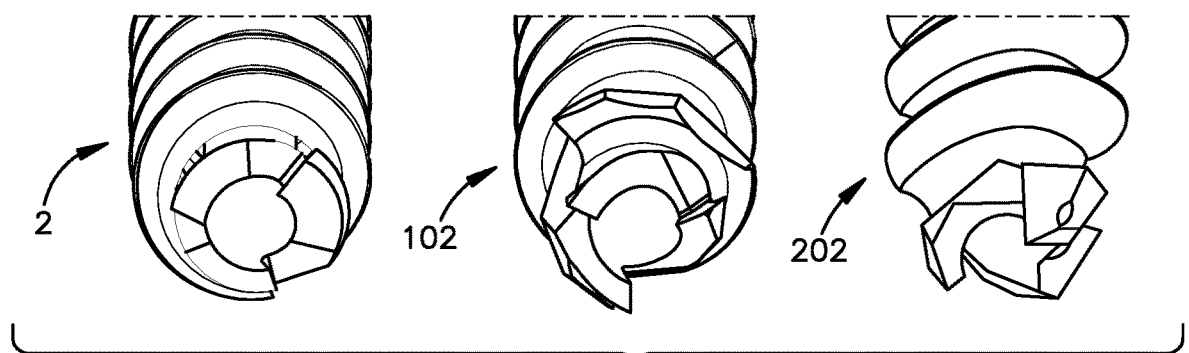
Fig.37

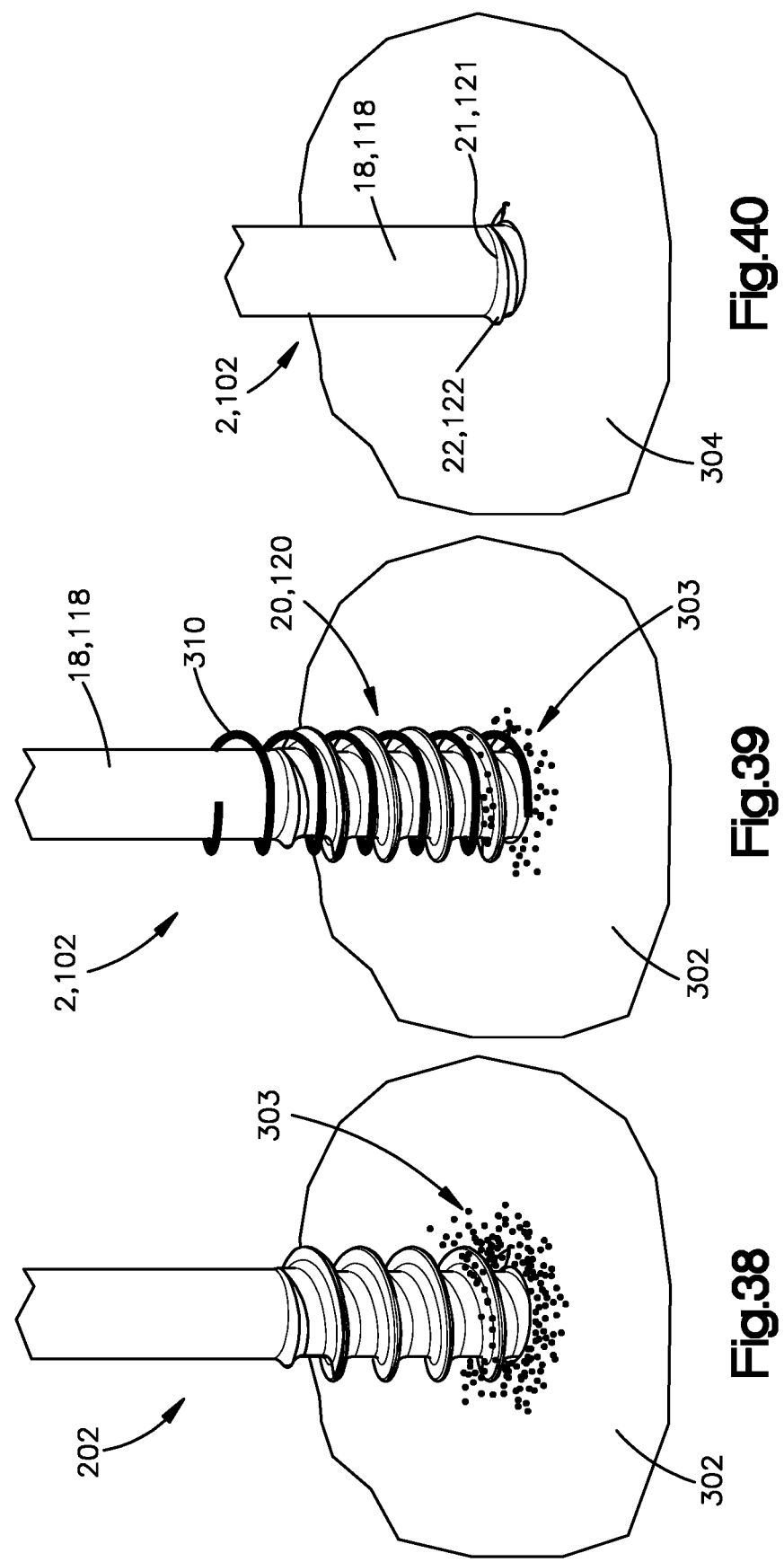

ANGLED FLUTES IN CANNULATED BONE SCREWS

CROSS-REFERENCE TO RELATED APPLICATIONS

This application is a continuation of U.S. patent application Ser. No. 15/958,541, filed Apr. 20, 2018, which claims the benefit of U.S. Provisional Patent Application Ser. No. 62/488,398, filed Apr. 21, 2017, in the name of Zastrozna, the entire disclosure of which is hereby incorporated by reference.

TECHNICAL FIELD

The present invention relates to a cannulated bone anchor having cutting flutes extending to the distal end of the bone anchor.

BACKGROUND

Bone fixation members, including cannulated bone screws, are conventionally utilized to anchor within bone material. A cannulation extending through a body of the bone screw can allow the bone screw to be guided along a guidewire or other guiding component to a target location within a bone. However, the cannulation can affect the ability of the distal end of the bone screw to penetrate or otherwise advance through bone material. Cannulated bone anchors have been adapted to include distal cutting flutes to facilitate insertion of the screw into bone.

SUMMARY

According to an embodiment of the present disclosure, a bone screw includes a proximal end and a distal end spaced from the proximal end in a distal direction along a longitudinal axis of the bone screw and a cannulation extending from the proximal end to the distal end. The bone screw further including a threaded region extending along at least a portion of a length of the screw, the length extending from the proximal end to the distal end. The threaded region defining at least one external thread that extends about the longitudinal axis along a helical path. The threaded region includes at least one flute that extends to the distal end of the bone screw. The at least one flute defines an associated at least one cutting tooth that, in turn, defines a cutting face oriented so as to define an angle with respect to the longitudinal axis. The angle is in the range of about 5 degrees and about 25 degrees, and the flute circumferentially interrupts at least a portion of the external thread.

According to another embodiment of the present disclosure, a bone screw includes a proximal end and a distal end spaced from the proximal end in a distal direction along a longitudinal axis of the bone screw. The bone screw includes a cannulation extending from the proximal end to the distal end and a threaded region extending along at least a portion of a length of the screw, the length extending from the proximal end to the distal end. The threaded region defines at least one external thread that extends about the longitudinal axis along a helical path. The threaded region includes a plurality of cutting flutes spaced circumferentially with respect to one another. Each of the plurality of cutting flutes extending to the distal end of the bone screw. The plurality of cutting flutes defining a plurality of teeth spaced circumferentially between the cutting flutes. Each of the plurality of teeth defining a cutting face oriented so as to define an angle with respect to the longitudinal axis, the angle in the range of about 5 degrees and about 25 degrees,

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 9 is another side view of the distal end of the cannulated bone screw of FIG. 1;

FIGS. 10 through 12 are additional perspective views of the distal end of the cannulated bone screw of FIG. 1;

FIG. 21 is a side view of the cannulated bone screw of FIG. 19;

FIG. 22 is a longitudinal sectional view of a threaded portion of a shaft of the cannulated bone screw of FIG. 19;

FIG. 23 is a longitudinal sectional view of a portion of a head of the cannulated bone screw of FIG. 19;

FIG. 37 is a graphical representation of test data performed on cannulated bone screws of the present disclosure;

FIG. 38 is a perspective view illustrating cutting fragments forming during insertion of a prior art cannulated bone screw into test foam material;

FIG. 39 is a perspective view illustrating a cutting filament forming during insertion of a cannulated bone screw of the present disclosure into test foam material; and FIG. 40 is another perspective view illustrating a cannulated bone anchor of the present disclosure being inserted into test foam material without generating cutting fragments.

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Figure 1:
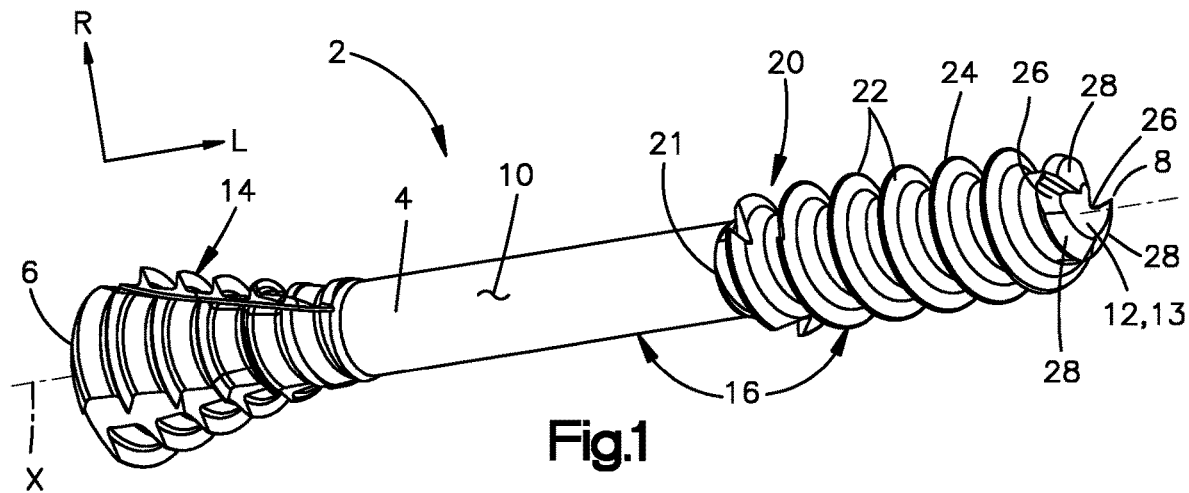
FIG. 1 is a perspective view of a cannulated bone screw, according to an embodiment of the present disclosure.
Figure 2:
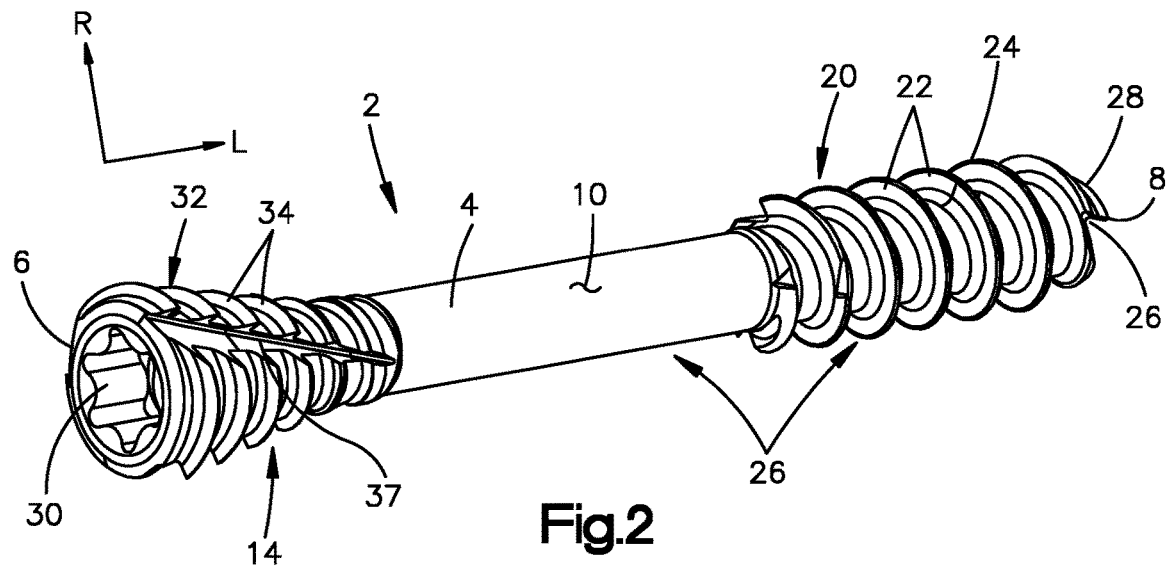
FIG. 2 is another perspective view of the cannulated bone screw of FIG. 1.

Referring to FIGS. 1 and 2, a cannulated bone screw 2 can be configured to engage and purchase within a bone in a clean and efficient manner that minimizes damage to the adjacent bone material. The cannulated bone screw 2 of the present disclosure has aggressive cutting features that provide strong initial bite at the commencement of insertion and further provide a predominant slicing cutting action (as opposed to a scraping cutting action) as the screw is advanced into bone, as discussed in more detail below.

The cannulated bone screw 2 can include a body 4 defining a proximal end 6 and a distal end 8 spaced from the proximal end 6 along a longitudinal axis X of the bone screw 2. The body 4 can define an outer surface 10 extending from the proximal end 6 toward the distal end 8. The longitudinal axis X can extend along a longitudinal direction L that is substantially perpendicular to a radial direction R. The radial direction R can be bi-directional, and can include mono-directional radially outward and radially inward components, wherein "radially outward" means in the radial direction R away from longitudinal axis X, and "radially inward" means in the radial direction R toward the longitudinal axis X. The bone screw 2 can also define a distal direction that extends from the proximal end 6 to the distal end 8 along the longitudinal axis X. The bone screw 2 can also define a proximal direction that extends from the distal end 8 to the proximal end 6 along the longitudinal axis X and is opposite the distal direction. It is to be appreciated that the distal and proximal directions are each mono-directional components of the bi-directional longitudinal direction L.

The body 4 can be formed of a bio-compatible material, such as titanium, a titanium alloy, stainless steel, or any combination thereof, by way of non-limiting example.

The screw body 4 can define a cannulation 12 extending through the body 4 from the proximal end 6 to the distal end 8. The cannulation 12 can be a through-bore that is configured to receive a guide wire therein in a manner allowing the bone screw 2 to move along the guide wire to a target location in tissue of a patient. An interior surface 13 of the body 4 within the cannulation 12 can be substantially smooth and cylindrical, although other geometries are within the scope of the present embodiments. The body 4 can also define a head 14 and a shaft 16 extending from the head 14 in the distal direction. The shaft 16 can include a shank 18 spaced from the head 14 in the distal direction. The shank 18 can be unthreaded. The shaft 16 can also include a threaded region 20 spaced from the shank 18 in the distal direction. The threaded region 20 of the shaft 16 can be referred to as a "threaded shaft region," and can extend from a threaded region proximal end 21 to the distal end 8 of the screw 2 along the longitudinal direction L. As shown, the threaded region proximal end 21 can be located at an interface between the shank 18 and the threaded shaft region 20, although the threaded region proximal end 21 could be positioned distally toward the head 14, on the head 14, or at the proximal end 6 of the bone screw 2. The threaded shaft region 20 can define or otherwise include an external thread 22 extending about the longitudinal axis X along a helical path 24. While the thread 22 can be a single-lead thread, as shown, it is to be appreciated that, in other embodiments, the thread 22 can be a double-lead thread. The helical path 24 can define a helix, and can thus be constant from the threaded region proximal end 21 to the distal end 8 of the bone screw 2. The thread 22 of the threaded shaft region 20 can be referred to as a "shaft thread." The shaft thread 22 can be configured to purchase within bone material, such as cortical and/or cancellous bone material, in a manner preventing the screw 2 from backing out of the bone.

The bone screw 2 can include one or more cutting features for cutting, penetrating and slicing bone material in a manner facilitating insertion of the bone screw 2 into bone. For example, the threaded shaft region 20 can include one or more cutting flutes 26 that extend through the screw body 4 to the distal end 8 of the bone screw 2. Each of the cutting flutes 26 can intersect the cannulation 12. The one or more cutting flutes 26 can define one or more cutting teeth 28 circumferentially spaced between the cutting flutes 26. Additionally, the cutting flutes 26 can circumferentially interrupt at least a portion of the shaft thread 22 as the thread 22 extends along the helical path 24. As shown, the bone screw 2 can include three (3) cutting flutes 26 and three (3) cutting teeth 28, although it is to be appreciated that other quantities of flutes 26 and teeth 28 are within the scope of the present disclosure.

Referring to FIG. 2, the head 14 can define a socket 30 extending from the proximal end 6 of the screw 2 in the distal direction. The socket 30 can be configured to receive a driving tool operated by a physician, and can have a star-hex configuration, although other socket configurations are within the scope of the disclosed embodiments. The head 14 can include a second threaded region 32 that includes threading 34 configured to engage bone, a bone plate, or other object as necessary. The threading 34 of the head 14 can extend from the proximal end 6 of the screw to a distal end 35 of the second threaded region 32. It is to be appreciated that the second threaded region 32 can be referred to as the "threaded head portion" and the threading 34 thereof can be referred to as "head threading." The head 14 can also define one or more cutting flutes 37 extending between the proximal end 6 of the screw 2 and the distal end 35 of the second threaded region 32.

Figure 3:
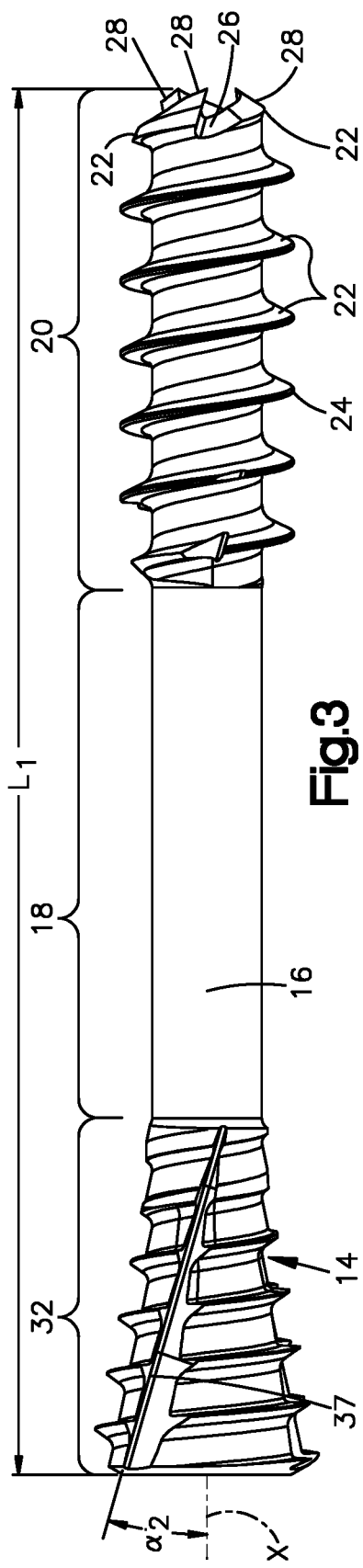
FIG. 3 is a side view of the cannulated bone screw of FIG. 1.

The cannulated bone screw 2 can be configured for insertion in bones of the forefoot, including phalanges and metatarsals, by way of non-limiting example. As shown in FIG. 3, the screw 2 can define a length Li, measured from the proximal end 6 to the distal end along the longitudinal direction L. The threaded shaft region 20 can extend along at least a portion of the length Li, as shown. However, in other embodiments, the threaded shaft region 20 can extend along the entire length Li. It is to be appreciated various characteristics of the screw 2, such as the length Li, for example, can be adjusted depending on the various types of bones to be engaged and the various types of fractures and other trauma to be repaired or otherwise treated without departing from the spirit of the disclosed embodiments.

Figure 4:
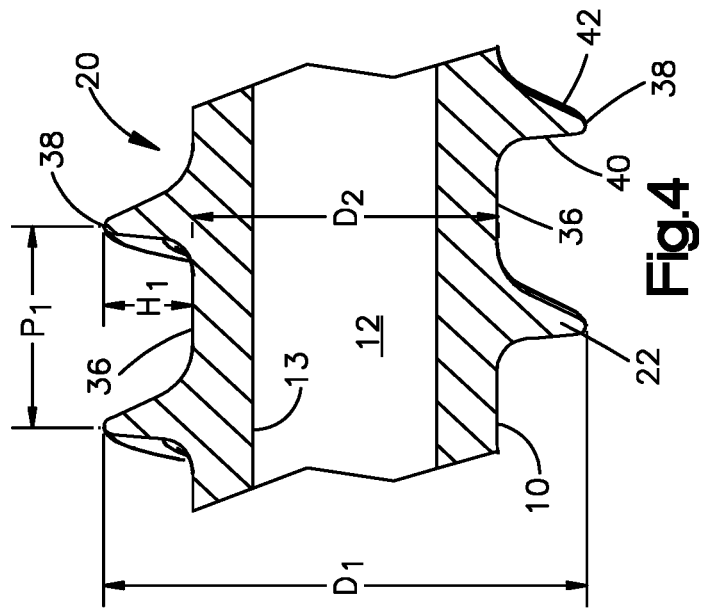
FIG. 4 is a longitudinal sectional view of a threaded portion of a shaft of the cannulated bone screw of FIG. 1.

Referring now to FIG. 4, each thread of the shaft thread 22 can extend radially outward from a root 36 to a crest 38 and can have a generally curved, convex profile at the crest 38. The root 36 can be characterized as the outer surface 10 of the bone screw 2 between the threads. It is to be appreciated that, with respect to the shaft thread 22, the term "thread" or "threading" as used herein refers to any portion of the screw 2 that extends outwardly from the root 36 with respect to the radial direction R.

The crest 38 of the shaft thread 22 can be aligned with the helical path 24. Each thread of the shaft thread 22 can define an undercut portion 40 extending proximally from the crest 38, and can further define a front slope 42 extending distally from the crest 38. The shaft thread 22 can have a thread height $H_1$ measured from root 36 to crest 38 along a direction orthogonal to the outer surface 10 of the bone screw 2 at the root 36. The thread height $H_1$ can be in the range of about 0.2 mm and about 0.9 mm, by way of non-limiting example. At the threaded shaft region 20, the direction orthogonal to the outer surface 10 extends along the radial direction R. The shaft thread 22 can define a major diameter $D_1$ at the crest 38 and a minor diameter $D_2$ at the root 36. The minor diameter $D_2$ can also define the diameter of the shank 18. For use with bones of the forefoot, the minor diameter can be in the range of about 2 mm to about 4 mm, although other diameters are within the scope of the present disclosure. The shaft thread 22 can have a thread pitch $P_1$ in the range of about 0.7 mm and about 2 mm, by way of non-limiting example.

Figure 5:
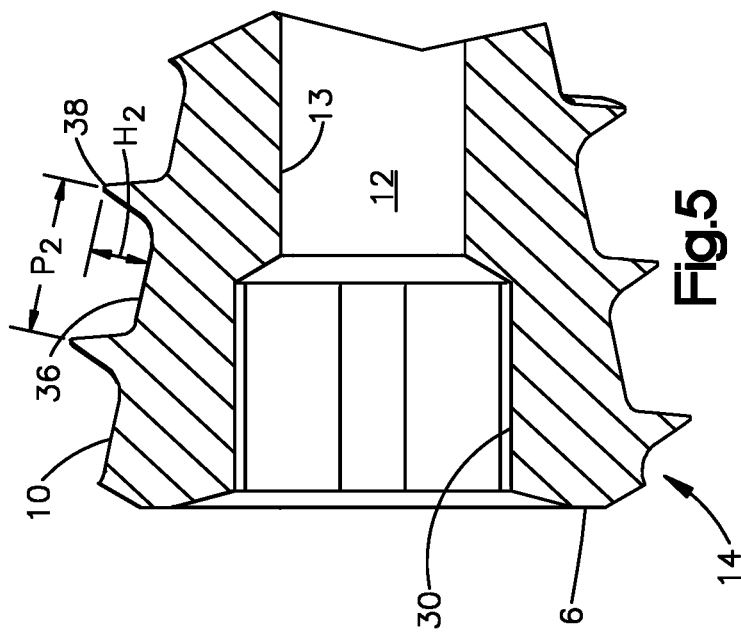
FIG. 5 is a longitudinal sectional view of a portion of a head of the cannulated bone screw of FIG. 1.

The head threading 34 can have different characteristics than the shaft thread 22. For example, the head threading 34 can have a different thread pitch and/or a different thread height than that of the shaft thread 22. In particular, as shown in FIG. 5, the second threading 34 can have a second thread pitch $P_2$ in the range of about 0.5 mm and about 1.5 mm, and a second thread height $H_2$ in the range of about 0.2 mm and about 0.6 mm.

A pitch ratio between the first and second threadings 22, 32 can be in the range of about 1.1:1 and about 1.8:1. Thus, the cannulated bone screw 2 can be configured such that, once the second threading 34 engages bone material, the first and second threadings 22, 32 will compress material between the head 14 and the threaded shaft region 20.

Figure 6A:
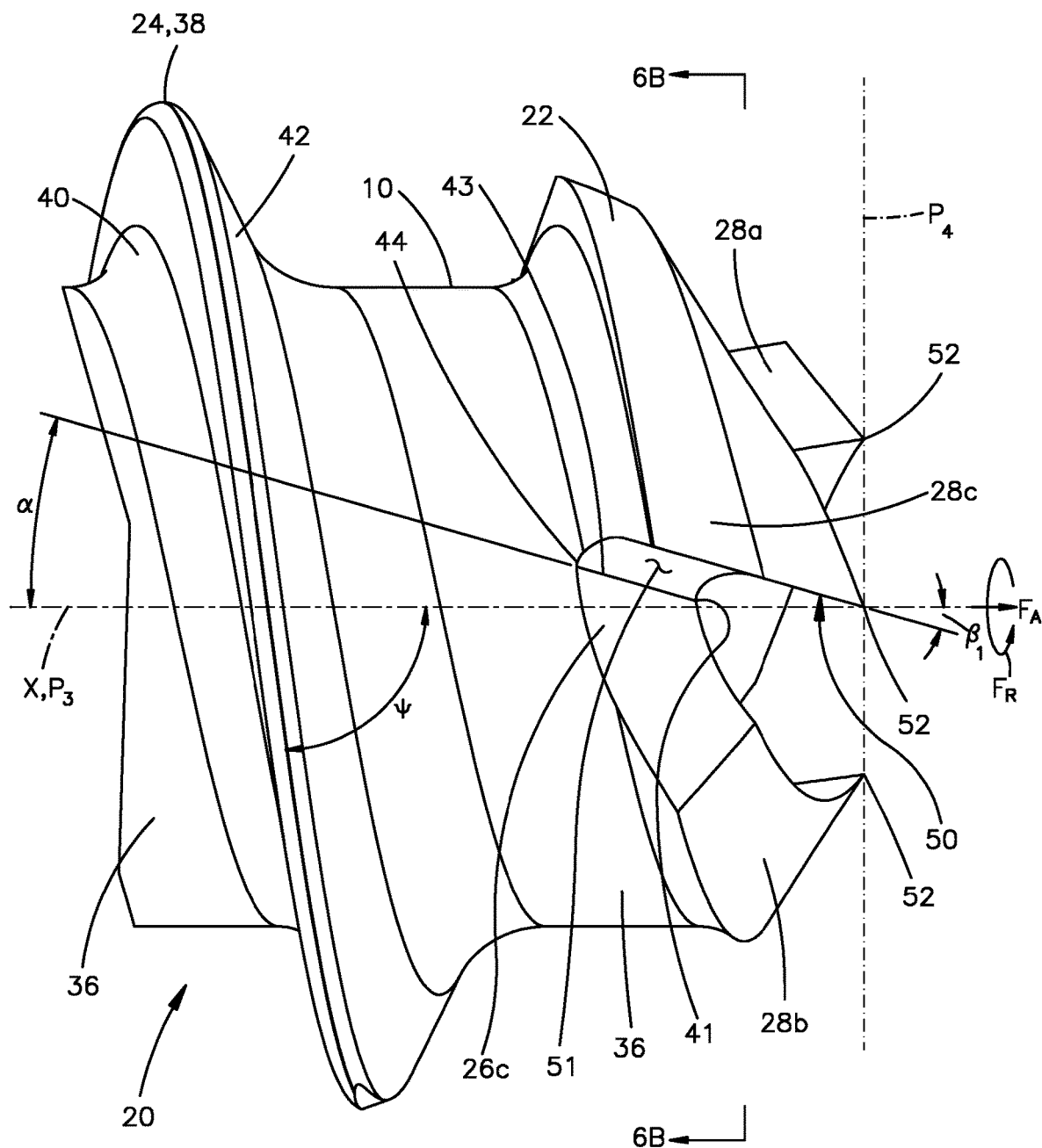
FIG. 6A is a side view of a distal end of the cannulated bone screw of FIG. 1.

Referring now to FIG. 6A, the helical path 24 can be oriented at a helix angle $\psi$ in the range of about 65 degrees and about 85 degrees, measured from the longitudinal axis X to the crest 38 of the shaft thread 22. In some embodiments, the helix angle $\psi$ can be in the range of about 78 and about 82 degrees. In other embodiments, the helix angle $\psi$ can be less than 65 degrees. In further embodiments, the helix angle $\psi$ can be greater than 85 degrees. The helix angle $\psi$ can optionally be uniform along the entire length of the threaded shaft region 20, including along the teeth 28 at distal end 8 of the bone screw 2.

The cutting flutes 26 and cutting teeth 28 can be configured to allow the teeth 28 to promptly bite into cortical bone material responsive to a driving force having a first, axial component $F_A$ along the longitudinal axis X and a second, rotational component $F_R$ about the longitudinal axis X. For example, each of the cutting flutes 26 can be oriented at a flute offset angle $\alpha$ that is offset from the longitudinal axis X of the bone screw 2. For example, the flute offset angle $\alpha$ can be in the range of about 5 degrees and about 25 degrees with respect to the longitudinal axis X. In additional embodiments, the flute offset angle $\alpha$ can be in the range of about 10 degrees and about 20 degrees. In other embodiments, the flute offset angle $\alpha$ can be in the range of about 14 degrees and about 18 degrees. In further embodiments, the flute offset angle $\alpha$ can be about 16 degrees. In yet further embodiment, the flute offset angle $\alpha$ can be in the range of about 25 degrees and about 60 or greater than 60 degrees. Additionally, each of the cutting flutes 26 can extend radially inward from the outer surface 10 of the screw body 4 to a flute trough 43. The flute trough 43 can intersect the cannulation 12 at a first or distal-most trough location 41 and can intersect the outer surface 10 of the screw body at a second or proximal-most trough location 44. It is to be appreciated that, as shown in FIG. 6A, the flute offset angle $\alpha$ can be defined by the path along which the flute trough 43 extends between the distal-most and proximal-most trough locations 41, 44. It is also to be appreciated that the cutting flutes 37 of the head thread 32 can also be oriented at a flute angle $\alpha_2$ in the range of about 5 degrees and about 25 degrees (FIG. 3).

With reference to FIGS. 6A through 8, the cutting flutes 26 and cutting teeth 28 can include a first tooth 28a, a second tooth 28b, and a third tooth 28c circumferentially spaced between a first flute 26a, a second flute 26b, and a third flute 26c, respectively. The first tooth 28a can rotationally lead the second tooth 28b, which can rotationally lead the third tooth, 28c, which can rotationally lead the first tooth 28a as the screw 2 rotates about the longitudinal axis X. Each tooth 28 can define a rotationally leading side 46 and a rotationally trailing side 48 opposite the leading side 46 with respect to a rotational direction Z of insertion of the screw 2. For example, the first flute 26a can be located at the rotationally leading side 46 of the first tooth 28a, while the second flute 26b can be located at a rotationally trailing side 48 of the first tooth 28a. Similarly, the second flute 26b can be located at a rotationally leading side 46 of the second tooth 28b, while the third flute 26c can be located at a rotationally trailing side 48 of the second tooth 28b. Moreover, the third flute 26c can be located at a rotationally leading side 46 of the third tooth 28c, while the first flute 26a can be located at a rotationally trailing side 48 of the third tooth 28c. It is to be appreciated that each flute trough 43 can separate (or, stated differently, define an interface between) the rotationally trailing side 48 of one tooth 28 and the rotationally leading side 46 of the next tooth. Additionally, the proximal-most trough location 44 (at which the flute trough 43 intersects the outer surface 10 of the body 4) can define the proximal end of the rotationally trailing side 48 of the one tooth 28 as well as the proximal end of the rotationally leading side 46 of the next tooth. Additionally, each tooth 28 can extend radially outward from the cannulation 12 to the outer surface 10 of the screw body 4.

Each cutting tooth 28 can also define a cutting surface or "cutting face" 50 (FIG. 7) on the rotationally leading side 46. The size, shape and orientation of the cutting face 50 can be defined by the flute 26 on the rotationally leading side 46 of the tooth 28. The cutting face 50 of each tooth 28 can optionally be substantially planar. The rotationally leading side 46 of each tooth 28 can also define a secondary surface 51 positioned between the cutting face 50 and the trough 43 of the rotationally leading flute 26. The secondary surface 51 can have a concave, curved profile joining the flute trough 43 with the cutting face 50. The cutting face 50 can be referred to as a primary cutting face of the associated tooth 28 and the secondary surface 51 can be referred to as a secondary cutting face of the tooth 28.

Each tooth 28 can include a cutting tip 52 at the distal terminus of the tooth 28. The cutting tip 52 can be a single point, as shown, although other geometries, such as a distal edge, are within the scope of the present disclosure. The cutting tip 52 can define the distal-most point of the associated cutting face 50. As shown in the present embodiment, the cutting tip 52 can be located at a radially inward edge of the tooth 28 and can thus also be positioned at the interior surface 13 of the screw body 4. The cutting tips 52 of the first, second, and third teeth 28a-28c can collectively define a second plane $P_4$ that is orthogonal to the longitudinal axis X of the bone screw 2 (FIG. 6A). Stated differently, the cutting tips 52 of each of the teeth 28 can be spaced from the proximal end 6 of the bone screw 2 at substantially the same distance along the longitudinal direction L. It is to be appreciated that the cutting tips 52 can each define the distal end 8 of the bone screw 2. Thus, by placing each of the cutting tips 52 against a surface (such as an outer surface of a target bone), the physician can gain a tactile indication of when the screw 2 is oriented substantially orthogonal to the surface.

FIG. 6A illustrates a non-limiting example of an orthogonal side view of the distal end 8 of the bone screw 2, with the third tooth 28c shown with the cutting tip 52 thereof directly overlying the longitudinal axis X. Thus, the longitudinal axis X of the screw 2 and the cutting tip 52 of the third tooth 28c can jointly define a longitudinal plane $P_3$ of the third tooth 28c. In FIG. 6, the longitudinal plane $P_3$ extends along the radial direction R directly into/out of the page. At this orientation, the cutting face 50 of the third tooth 28c can also extend along the radial direction R directly into/out of the page. The cutting face 50 of the third tooth 28c can be oriented at a first rake angle $\beta_1$ with respect to the longitudinal plane $P_3$ of the third tooth 28c. The first rake angles $\beta_1$ of the cutting faces 50 of the first and second teeth 28a, 28b can be defined in like manner. For example, the cutting face 50 of the first tooth 28a can be oriented at a first rake angle $\beta_1$ with respect to a longitudinal plane defined by the longitudinal axis X and the cutting tip 52 of the first tooth 28a. Similarly, the cutting face 50 of the second tooth 28b can be oriented at a first rake angle $\beta_1$ with respect to a longitudinal plane defined by the longitudinal axis X and the cutting tip 52 of the second tooth 28b.

As the cutting face 50 can effectively be defined by the geometry of the associated, rotationally leading flute 26, it is to be appreciated that the first rake angle $\beta_1$ and the flute offset angle $\alpha$ can be substantially equivalent. Thus, each cutting face 50 can have a first rake angle $\beta_1$ in the range of about 5 degrees and about 25 degrees with respect to the longitudinal axis X. In additional embodiments, the first rake angle $\beta_1$ can be in the range of about 10 degrees and about 20 degrees. In other embodiments, the first rake angle $\beta_1$ can be in the range of about 14 degrees and about 18 degrees. In further embodiments, the first rake angle $\beta_1$ can be about 16 degrees. In yet further embodiment, the first rake angle $\beta_1$ can be in the range of about 25 degrees and about 60 or greater than 60 degrees. It is to be appreciated that the first rake angle $\beta_1$ can be different (i.e., greater or less than) the flute offset angle $\alpha$.

Figure 6B:
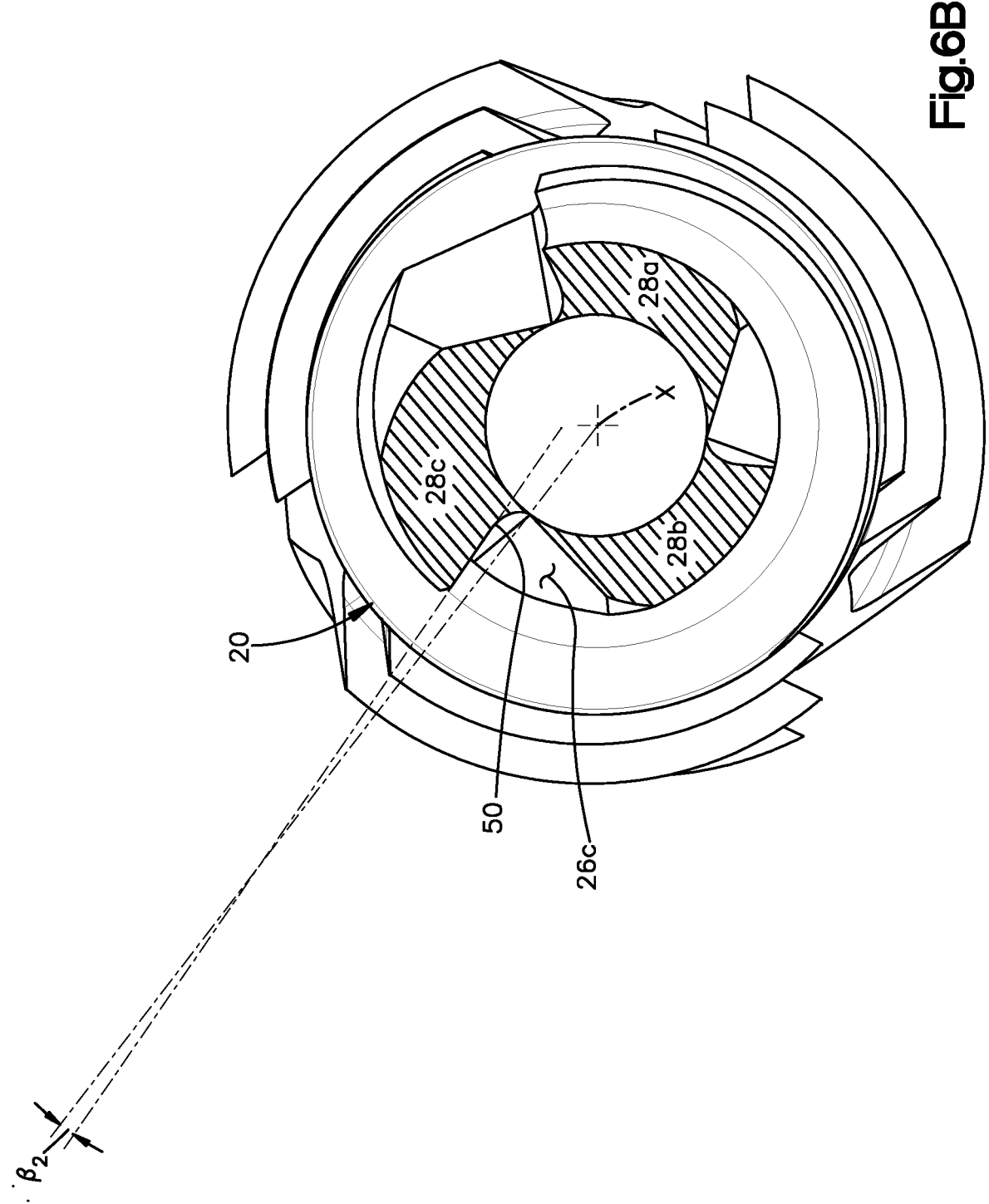
FIG. 6B is a sectional end view of the distal end of the cannulated bone screw, taken along section line 6B-6B in FIG. 6A.

As shown in FIG. 6B, the orientation of the cutting face 50 of each tooth 28a, 28b, 28c can also define a second rake angle $\beta_2$ with respect to a reference line intersecting the longitudinal axis X and the radially outermost edge of the cutting face 50 in a reference plane orthogonal to the longitudinal axis X. Preferably, the second rake angle $\beta_2$ is a positive rake angle.

The cutting tip 52 and the first and second rake angles $\beta_1$, $\beta_2$ of the cutting face 50 of each tooth 28 can allow each tooth 28 to promptly bite into (i.e., penetrate) and advance through cortical bone material responsive to the driving force without undue scraping or twisting of the screw 2 against the bone. Thus, the teeth 28 can provide the screw 2 with self-drilling functionality.

In addition to biting or penetrating, each of the cutting teeth 28 can define one or more cutting edges for slicing, splitting, cleaving, dividing, and otherwise separating bone material during insertion of the screw 2. For example, FIG. 9 illustrates the distal end 8 of the bone screw 2 with the third tooth 28c generally oriented at the top of the figure. As shown with respect to the third tooth 28c, each tooth 28 can define a first cutting edge 54 extending from the cutting tip 52 generally in the proximal direction. The first cutting edge 54 can be located at an interface between the cutting face 50 and the interior surface 13 of the body 4. The first cutting edge 54 can be oriented or otherwise configured to slice or otherwise cleave bone material along a direction that is substantially tangential to the radial direction R. Stated differently, if the bone screw 2 were inserted within a bone and rotated about the longitudinal axis without being advanced distally, the first cutting edge 54 could cut a substantially cylindrical kerf in the bone material about the longitudinal axis X.

With continued reference to FIG. 9, each tooth 28 can also define a second cutting edge 56 extending radially outwardly and proximally from the cutting tip 52 to the outer surface 10 of the screw body 4. A proximal end 58 of the second cutting edge 56 can be at the outer surface 10 of the screw body 4. The cutting tip 52 can define the distal end of the second cutting edge 56. The second cutting edge 56 can be oriented so as to define a cutting edge angle θ of the associated tooth 28 with respect to the second plane $P_4$. The second cutting edge 56 can be oriented or otherwise configured to slice or otherwise cleave bone material along the distal direction as the screw 2 is advanced. For example, if the bone screw 2 were advanced through bone material along the distal direction without any rotation about the longitudinal axis X, the second cutting edge 56 could cut a substantially linear kerf oriented along the longitudinal direction L. However, as the screw 2 is both rotated and advanced distally during insertion, each of the first and second cutting edges 54, 56 slices or otherwise cleaves bone material along a helical path. It is to be appreciated that, at least in part due to the rake angles $\beta_1$, $\beta_2$ of the cutting face 50, the first and second cutting edges 54, 56, as well as a third cutting edge 63 (described more fully below with reference to FIG. 13) can effectively separate bone material by a slicing separation mechanism that substantially does not include a scraping or shearing separation mechanism.

Figure 7:
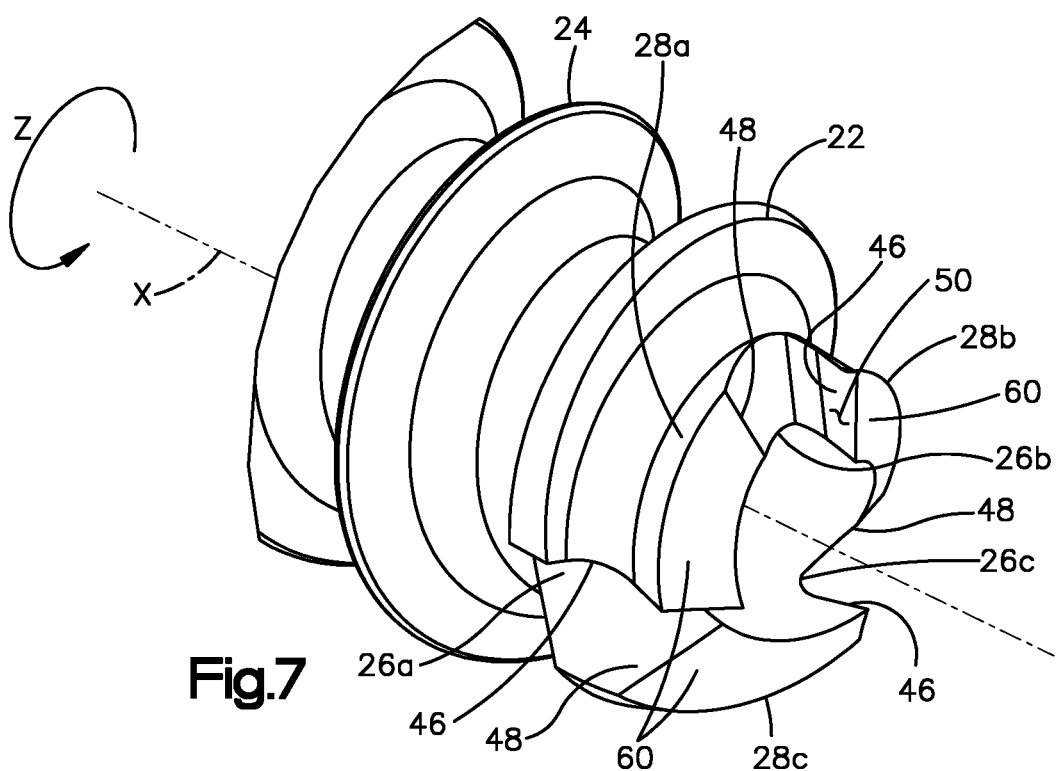
FIG. 7 is a perspective view of the distal end of the cannulated bone screw of FIG. 1.
Figure 8:
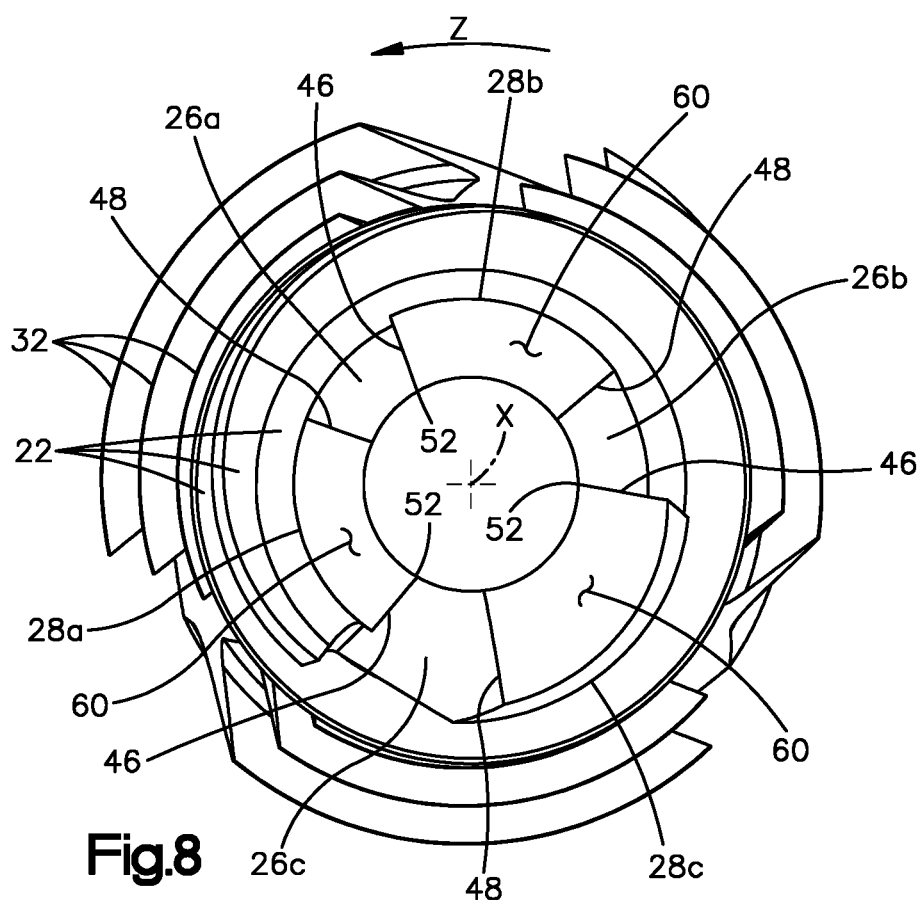
FIG. 8 is an end view of the distal end of the cannulated bone screw of FIG. 1.

Each tooth 28 can also define a relief surface 60 extending from the rotationally leading side 46 to the rotationally trailing side 48 of the tooth 28, as also shown in FIGS. 7 and 8. At the cutting face 50, the second cutting edge 56 can define the rotationally leading edge of the relief surface 60. The cutting edge angle θ can optionally be consistent from the rotationally leading side 46 to the rotationally trailing side 48 of the tooth 28; however, other geometries are within the scope of the present disclosure. The relief surface 60 can extend generally helically from the second cutting edge 56 proximally about the longitudinal axis X. Accordingly, the relief surfaces 60 of the teeth 28 can be termed "helical" relief surfaces. In other embodiments, however, the relief surfaces 60 of the teeth 28 can be substantially planar, whereby such planar relief surfaces can be termed "straight" relief surfaces. In such embodiments, the straight relief surfaces can be formed by milling or otherwise planarizing the helical relief surfaces 60 shown in FIG. 9

FIGS. 10 through 12 illustrate additional perspective views of the cutting teeth 28 at the distal end 8 of the bone screw 2. In FIG. 10, the first tooth 28a is oriented at the top of the view. In FIG. 11, the second tooth 28b is oriented at the top of the view. In FIG. 12, the third tooth 28c is oriented at the top of the view. As can be seen in FIGS. 7 through 12, each of the first, second, and third teeth 28a-28c can define at least a portion of the shaft thread 22. As set forth above, the helix angle ψ can be uniform along the entire length of the threaded shaft region 20, including along the teeth 28.

Figure 14:
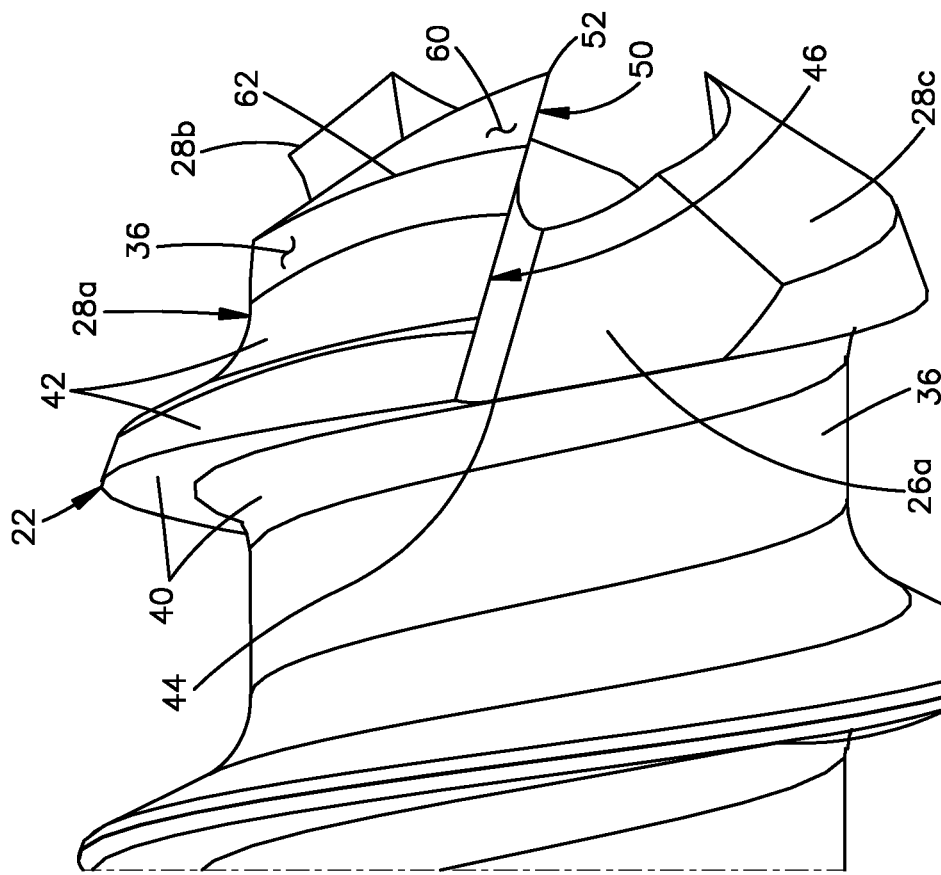
FIG. 14 is a side view of the distal end of the cannulated bone screw with the first cutting tooth rotated toward a center of the view.
Figure 13:
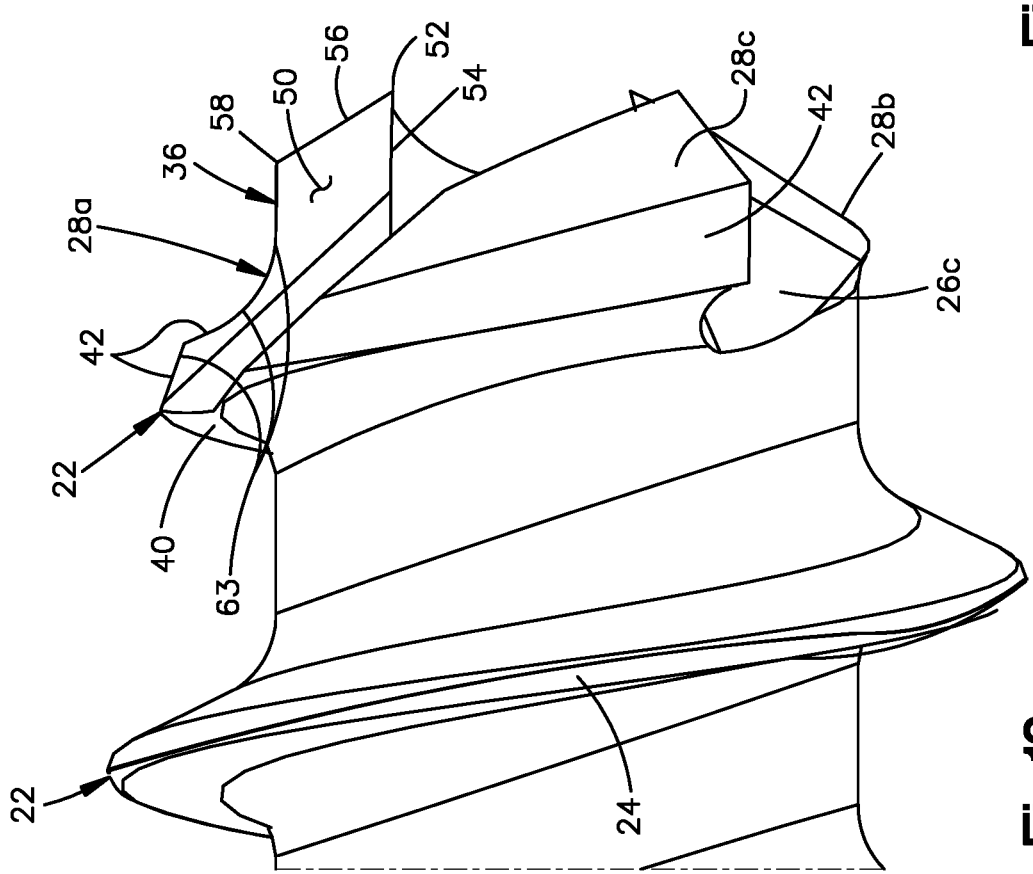
FIG. 13 is a side view of the distal end of the cannulated bone screw with a first cutting tooth positioned near the top of the view.
Figure 16:
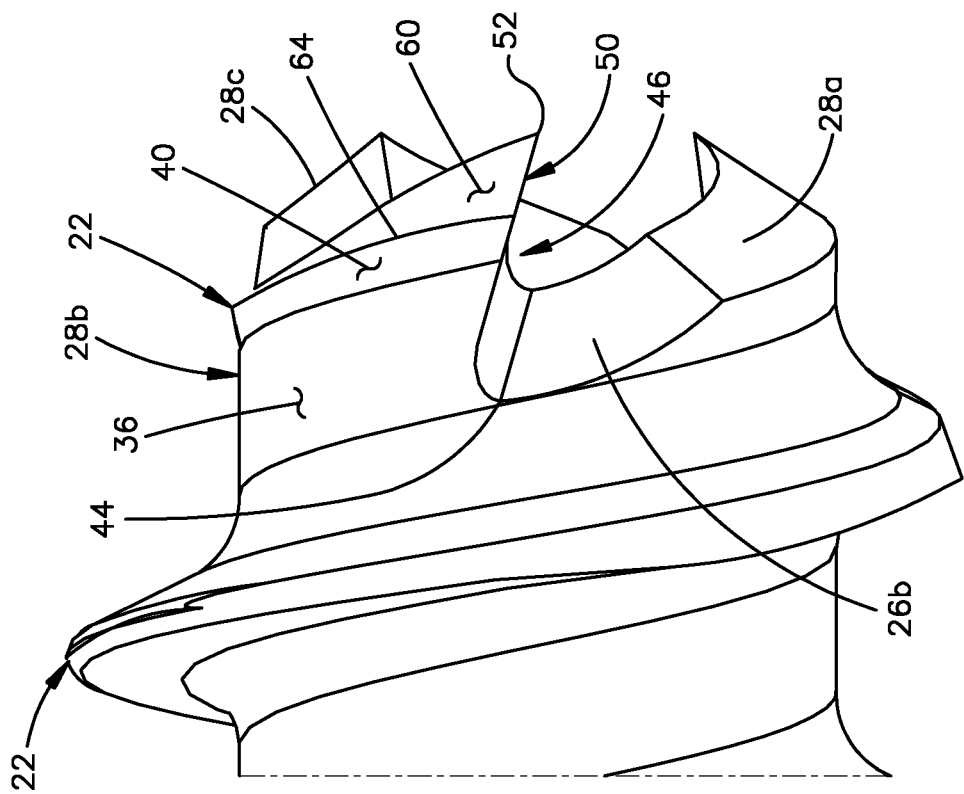
FIG. 16 is a side view of the distal end of the cannulated bone screw with the second cutting tooth rotated toward a center of the view.
Figure 15:
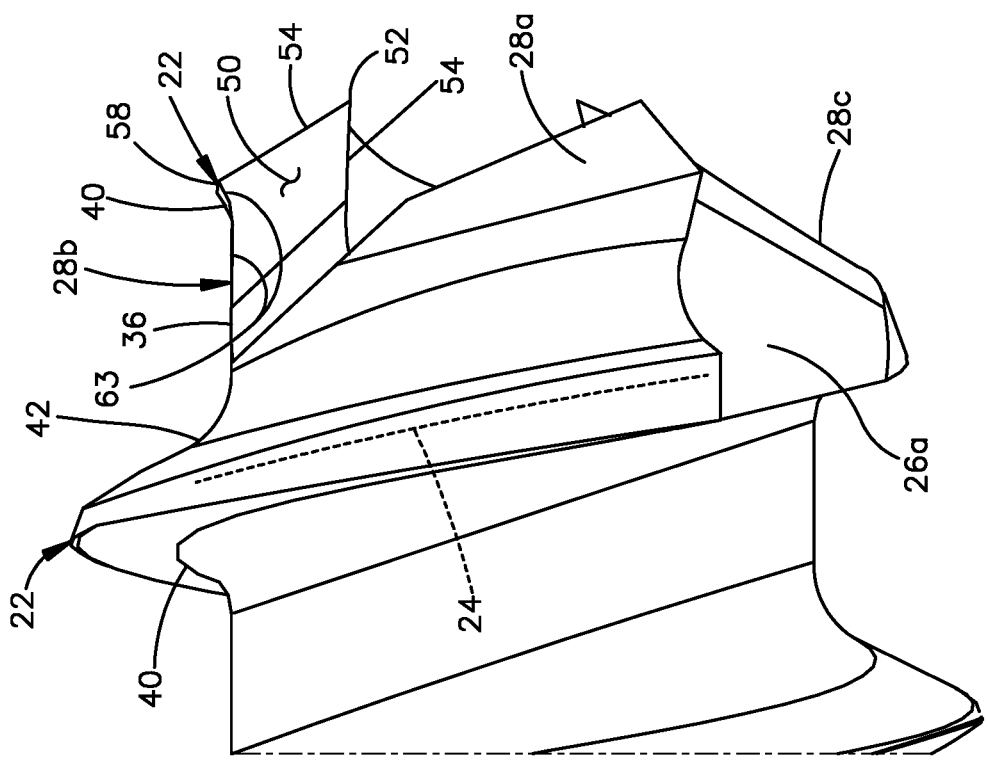
FIG. 15 is a side view of the distal end of the cannulated bone screw with a second cutting tooth positioned near the top of the view.
Figure 18:
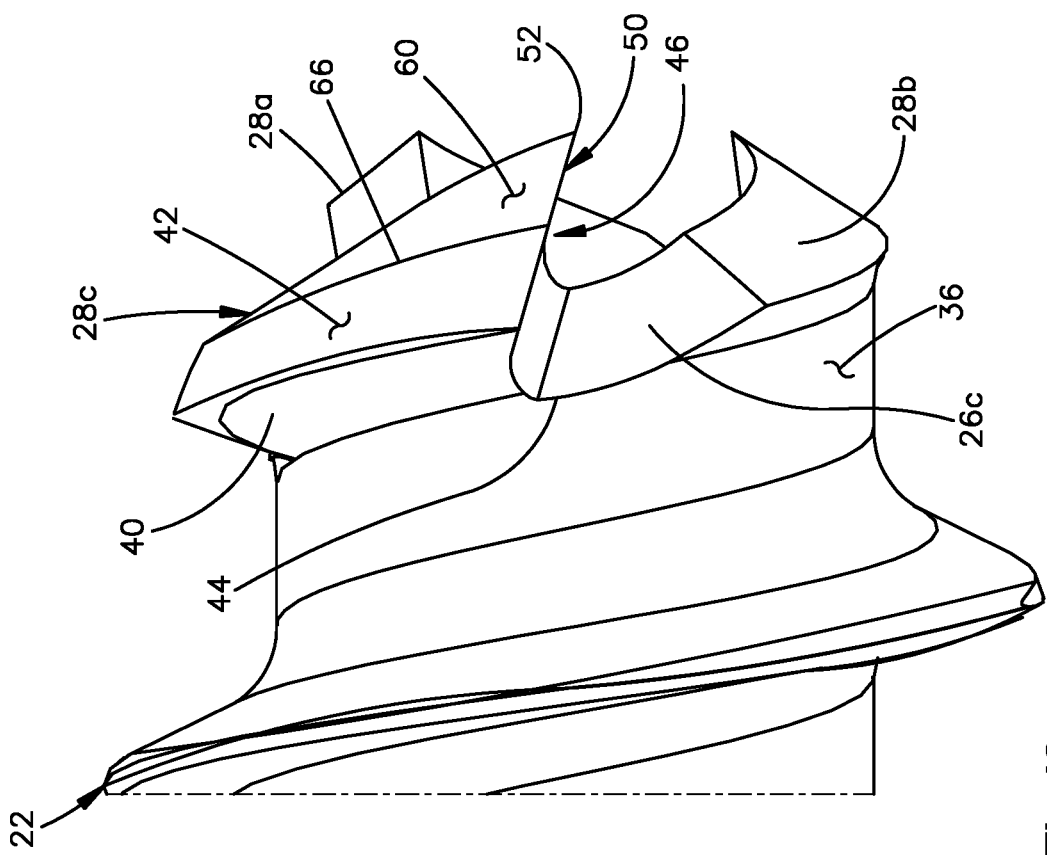
FIG. 18 is a side view of the distal end of the cannulated bone screw with the third cutting tooth rotated toward a center of the view.
Figure 17:
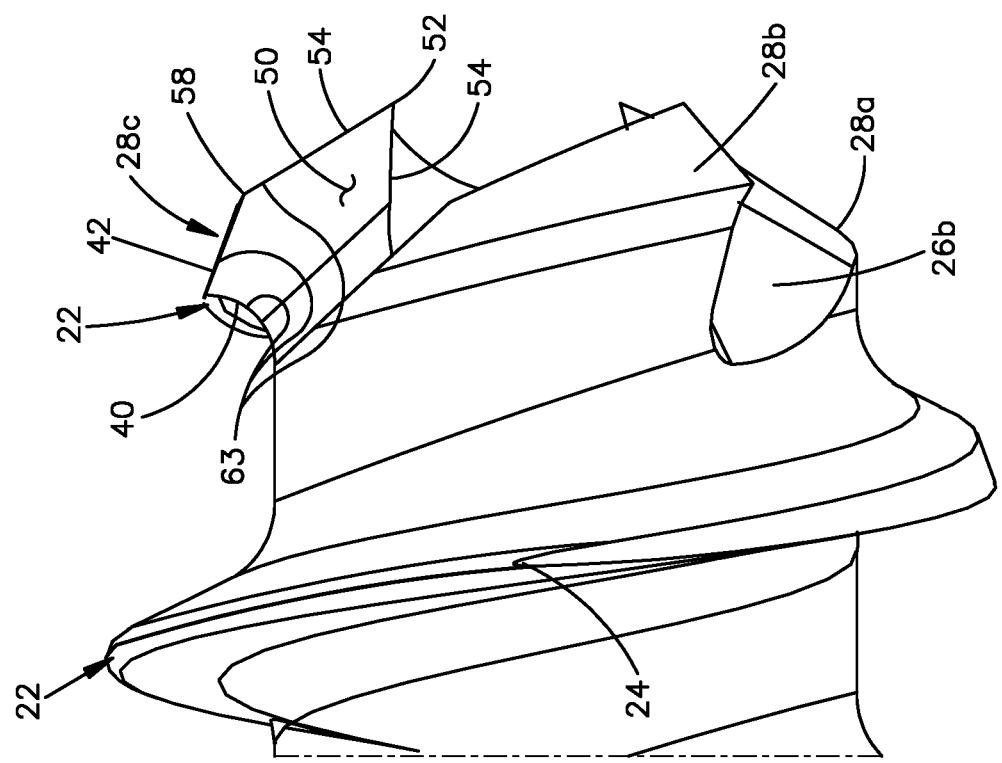
FIG. 17 is a side view of the distal end of the cannulated bone screw with a third cutting tooth positioned near the top of the view.

Referring now to FIGS. 13 through 18, the configuration and operation of the teeth 28 will be further discussed. FIGS. 13 and 14 illustrate the first tooth 28a as it rotates from the top of the view (FIG. 13) to a point where the cutting face 50 extends perpendicularly into the page (FIG. 14). FIGS. 15 and 16 illustrate the second tooth 28b as it rotates from the top of the view (FIG. 15) to a point where the cutting face 50 extends perpendicularly into the page (FIG. 16). FIGS. 17 and 18 illustrate the third tooth 28c as it rotates from the top of the view (FIG. 17) to a point where the cutting face 50 extends perpendicularly into the page (FIG. 18).

As shown in FIGS. 13 and 14, the first tooth 28a can define a portion of the shaft thread 22. In particular, a third cutting edge 63 of the cutting face 50 of the first tooth 28a can define at least a front slope 42 thread portion and a root 36 portion spaced distally from the front slope 42 thread portion. Additionally, on the first tooth 28a, the proximal end 58 of the second cutting edge 56 can be located at the root 36 portion. The front slope 42 thread portion, the root 36 portion, and the relief surface 60 of the first tooth 28a can each extend helically in the proximal direction from the leading side 46 to the trailing side 48 of the first tooth 28a. The root 36 can be contiguous with the relief surface 60 of the first tooth 28a at an edge 62. The third cutting edge 63 can provide the first tooth 28a with self-tapping functionality.

As shown in FIGS. 15 and 16, the second tooth 28b can also define a portion of the shaft thread 22. In particular, a third cutting edge 63 of the cutting face 50 of the second tooth 28b can define a root 36 portion and an undercut 40 thread portion spaced distally from the root 36 portion. Additionally, the proximal end 58 of the second cutting edge 56 can be located at the undercut 40 thread portion. Thus, on the second tooth 28b, the proximal end 58 of the second cutting edge 56 can be located radially outward of the root 36. As shown in FIG. 16, the root 36, the undercut 40 thread portion, and the relief surface 60 can each extend helically in the proximal direction from the leading side 46 to the trailing side 48 of the second tooth 28b. On the second tooth 28b, an edge 64 can define an interface between the relief surface 60 and the undercut 40 thread portion. The third cutting edge 63 can provide the second tooth 28b with self-tapping functionality.

As shown in FIGS. 17 and 18, the third tooth 28c can also define a portion of the shaft thread 22. In particular, a third cutting edge 63 of the cutting face 50 of the third tooth 28c can define a root 36 portion, an undercut 40 thread portion spaced distally from the root portion 36, and a front slope 42 thread portion spaced distally from the undercut 40 thread portion. Thus, on the third tooth 28c, the proximal end 58 of the second cutting edge 56 can be located radially outward of the root 36. As shown in FIG. 18, the root 36 portion, the undercut 40 thread portion, the front slope 42 thread portion, and the relief surface 60 can each extend helically in the proximal direction from the leading side 46 to the trailing side 48 of the third tooth 28c. Additionally, on the third tooth 28c, an edge 66 can define an interface between the relief surface 60 and the front slope 42 thread portion. The third cutting edge 63 can provide the third tooth 28c with self-tapping functionality.

Thus, the shaft thread 22 can essentially extend distally along the helical path 24 from the proximal end of the first tooth 28a to a position at least adjacent the cutting tip 52 of the third tooth 28c. The shaft thread 22 can intersect at least a portion of each of the cutting faces 50 of the teeth 28 so that the external thread 22 defines at least a portion of each cutting face 50. As the axial and rotational components $F_A$, $F_R$ of the drive force are applied and the bone screw 2 is driven into bone, the third cutting edge 63 of the first tooth 28a can form within the bone material a first helical channel through which at least a portion the shaft thread 22 can extend. Additionally, the third cutting edge 63 of the second tooth 28b can form within the bone material a second helical channel through which at least a portion of the shaft thread 22 can extend. Furthermore, the third cutting edge 63 of the third tooth 28c can form within the bone material a third helical channel through which at least a portion of the shaft thread 22 can extend. As the bone screw 2 makes a full revolution (i.e., 360 degrees about the longitudinal axis X) while being advanced distally into the bone material, the first, second, and third channels can merge into a substantially single helical channel through which the shaft thread 22 can extend as the screw 2 continues to advance.

Figure 19:
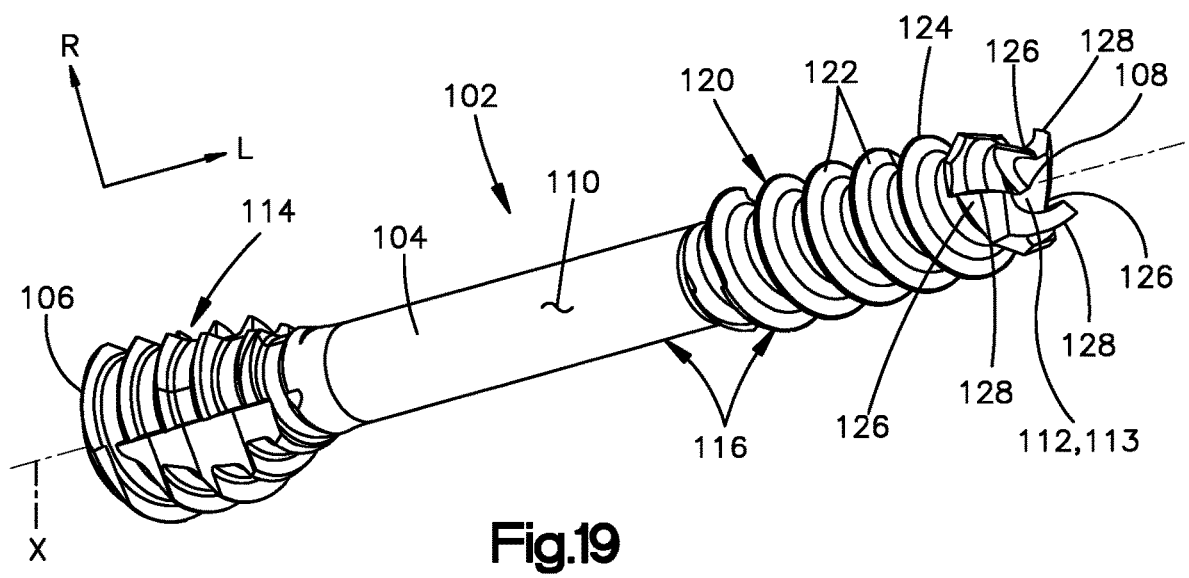
FIG. 19 is a perspective view of a cannulated bone screw, according to an embodiment of the present disclosure.
Figure 20:
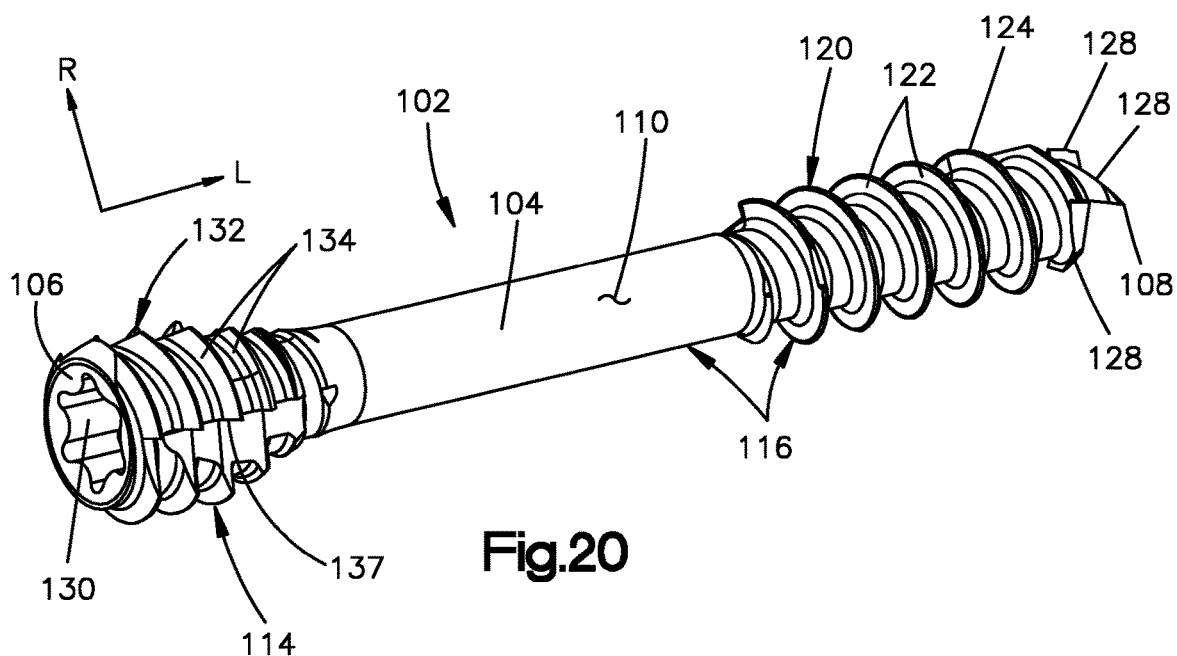
FIG. 20 is another perspective view of the cannulated bone screw of FIG. 19.

Referring now to FIGS. 19 and 20, a cannulated bone screw 102 can be configured according to a second embodiment of the present disclosure. The bone screw 102 can be configured similarly to the bone screw 2 of FIGS. 1 through 18, and can also be configured for insertion in bones of the forefoot, including phalanges and metatarsals, by way of non-limiting example. The bone screw can include a body 104 defining a proximal end 106 and a distal end 108 spaced from the proximal end 106 along the longitudinal axis X of the bone screw 102. The body 104 can define an outer surface 110 extending from the proximal end 106 toward the distal end 108.

An interior surface 113 of the screw body 104 can define a cannulation 112 extending through the body 104 from the proximal end 106 to the distal end 108. The body 104 can also define a head 114 and a shaft 116 extending from the head 114 in the distal direction. The shaft 116 can include a shank 118 spaced from the head 114 in the distal direction and a threaded shaft region 120 spaced from the shank 118 in the distal direction. The threaded shaft region 120 can define or otherwise include an external thread 122 extending about the longitudinal axis X along a helical path 124. The helical path 124 can define a helix, and can thus be constant along the length of the threaded shaft region. The shaft thread 122 can be configured to purchase within bone material, such as cortical and/or cancellous bone material, in a manner preventing the screw 102 from backing out of the bone.

The threaded shaft region 120 can include one or more cutting flutes 126 and one or more cutting teeth 128 circumferentially spaced between the cutting flutes 126. In the present embodiment, the geometry of the teeth 128 can be different than that of the embodiment illustrated in FIGS. 1 through 18, as set forth in more detail below.

The head 114 can define a socket 130 and can include a second threaded region 132 that includes head threading 134 configured to engage bone, a bone plate, or other object as necessary.

As shown in FIG. 21, the screw 102 can define a length $L_i$, measured from the proximal end 106 to the distal end 108 along the longitudinal direction L. As shown in FIG. 22, the shaft thread 22 can extend radially outward from a root 136 to a crest 138 and can have a generally curved, convex profile at the crest 138. The crest 138 can be aligned with the helical path 124. The shaft thread 122 can define an undercut portion 140 extending proximally from the crest 138 and a front slope 142 extending distally from the crest 138. The shaft thread 122 can have a thread height $H_1$ measured from root 136 to crest 138 along a direction orthogonal to the outer surface 110 of the bone screw 102 at the root 136. The thread height $H_1$ can be in the range of about 0.2 mm and about 0.9 mm, by way of non-limiting example. The shaft thread 122 can also define a major diameter $D_1$ at the crest 138 and a minor diameter $D_2$ at the root 136, which can also define the diameter of the shank 118. For use with bones of the forefoot, the minor diameter can be in the range of about 2 mm to about 4 mm, although other diameters are within the scope of the present disclosure. The shaft thread 122 can have a thread pitch $P_1$ in the range of about 0.7 mm and about 2 mm, by way of non-limiting example.

The head threading 134 can have different characteristics than the shaft thread 122. For example, the head threading 134 can a different thread pitch and/or a different thread height than that of the shaft thread 122. In particular, as shown in FIG. 23, the second threading 134 can have a second thread pitch $P_2$ in the range of about 0.5 mm and about 1.5 mm, and a second thread height $H_2$ in the range of about 0.2 mm and about 0.6 mm. A pitch ratio between the first and second threadings 122, 132 can be in the range of about 1.1:1 and about 1.8:1. Thus, the cannulated bone screw 102 can be configured such that, once the second threading 134 engages bone material, the first and second threadings 122, 132 will compress material between the head 114 and the threaded shaft region 120.

Figure 24:
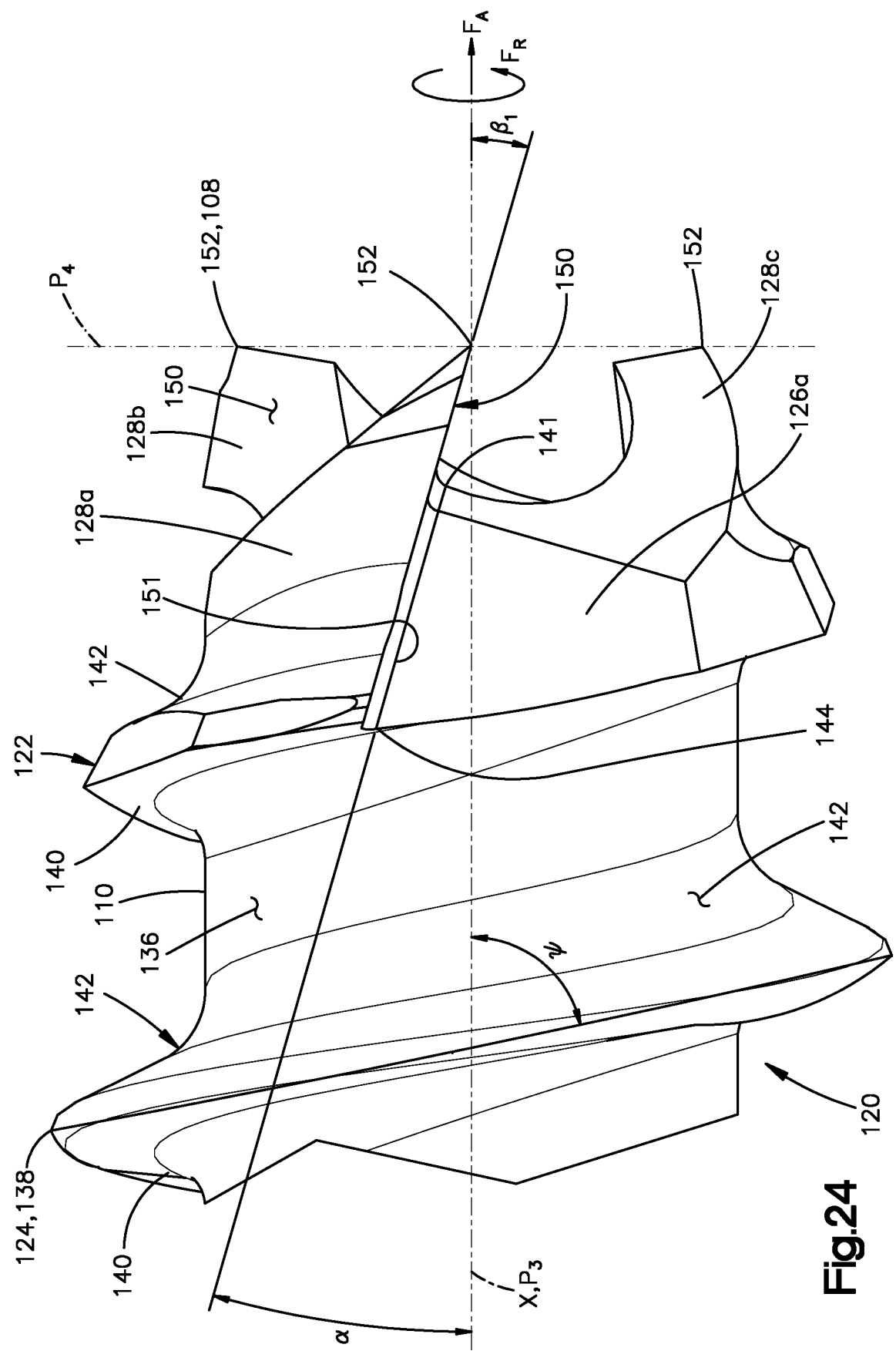
FIG. 24 is a side view of a distal end of the cannulated bone screw of FIG. 19.

Referring now to FIG. 24, the helical path 124 can be oriented at a helix angle ψ in the range of about 65 degrees and about 85 degrees, measured from the longitudinal axis X to the crest 138 of the shaft thread 122. The helix angle ψ can optionally be uniform along the entire length of the threaded shaft region 120, including along the teeth 28 at distal end 8 of the bone screw 102.

Additionally, the cutting flutes 126 and cutting teeth 128 can be configured to allow the teeth 128 to promptly bite into cortical bone material responsive to the axial and rotational components $F_A$, $F_R$ of the driving force. For example, each of the cutting flutes 126 can be oriented at a flute offset angle α that is offset from the longitudinal axis X of the bone screw 102, as described above. For example, the flute offset angle α can be in the range of about 5 degrees and about 25 degrees or up to 60 degrees or greater with respect to the longitudinal axis X. Additionally, each of the cutting flutes 126 can extend radially inward from the outer surface 110 of the screw body 104 to a flute trough 143. The flute trough 143 can intersect the cannulation 112 at a first or distal-most trough location 141 and can intersect the outer surface 110 of the screw body 104 at a second or proximal-most location 144. As described above, the flute offset angle α can be defined by the path along which the flute trough 143 extends between the distal-most and proximal-most trough locations 141, 145.

Figure 25:
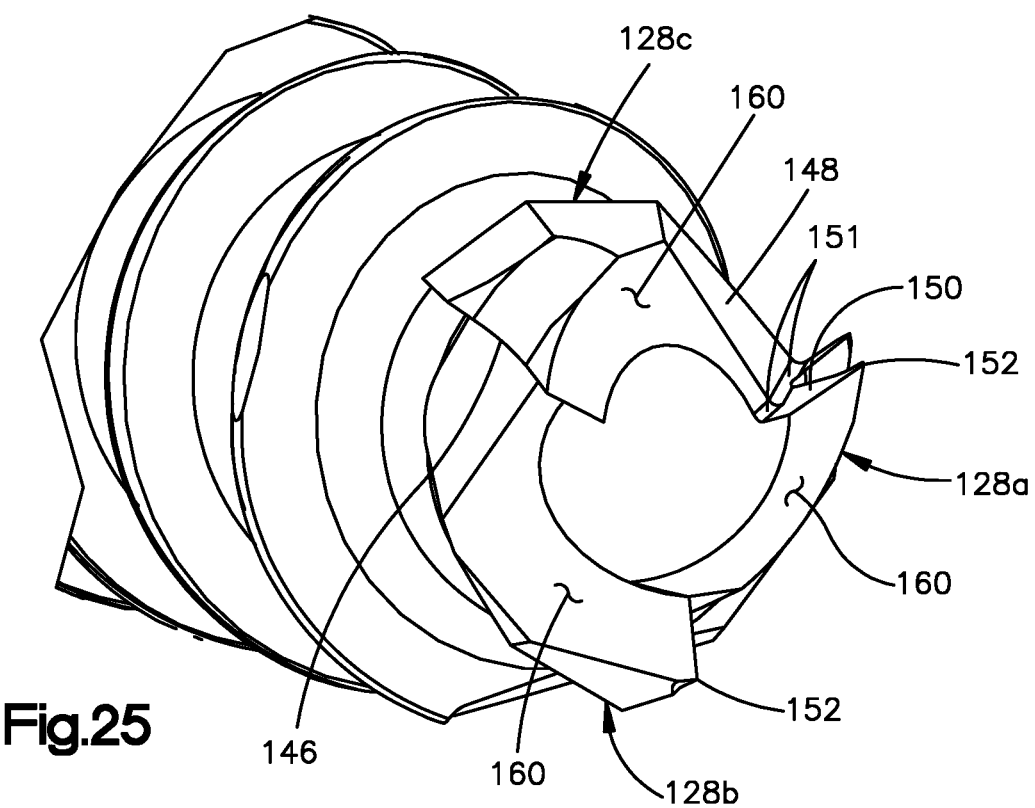
FIG. 25 is a perspective view of the distal end of the cannulated bone screw of FIG. 1.
Figure 26:
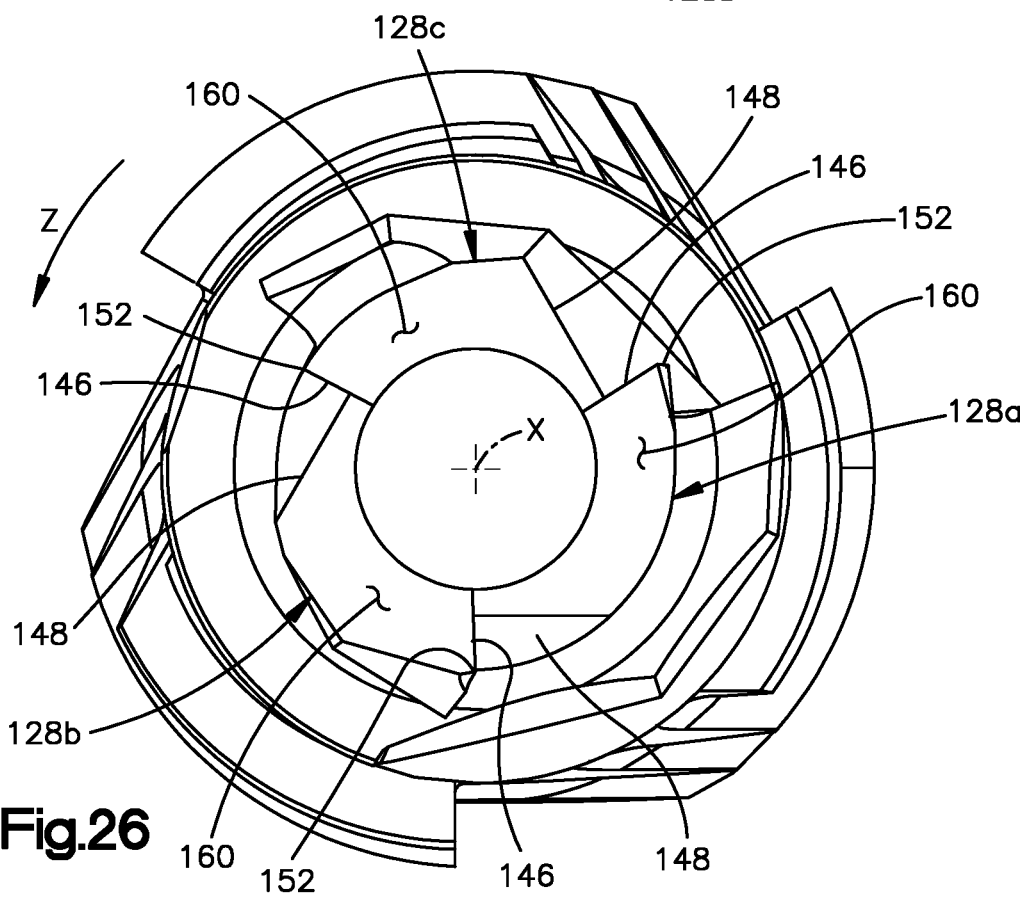
FIG. 26 is an end view of the distal end of the cannulated bone screw of FIG. 19.

With reference to FIGS. 24 through 26, the cutting flutes 126 and cutting teeth 128 can include a first tooth 128a, a second tooth 128b, and a third tooth 128c circumferentially spaced between a first flute 126a, a second flute 126b, and a third flute 126c, respectively. Each tooth 128 can define a rotationally leading side 146 and a rotationally trailing side 148 opposite the leading side 146 with respect to a rotational direction Z of insertion of the screw 102. Each flute trough 143 can separate the rotationally trailing side 148 of one tooth 128 and the rotationally leading side 146 of the next tooth. Additionally, the location 144 at which the flute trough 143 intersects the outer surface 110 of the body 104 can define the proximal end of the rotationally trailing side 148 of the one tooth 128 as well as the proximal end of the rotationally leading side 146 of the next tooth. Additionally, each tooth 128 can extend radially outward from the cannulation 112 to the outer surface 110 of the screw body 104. Each tooth 128 can define a relief surface 160 extending from the rotationally leading side 146 to the rotationally trailing side 148 of the tooth 128.

Each cutting tooth 128 can also define a cutting face 150 on the rotationally leading side 146. The cutting face 150 can optionally be substantially planar. The rotationally leading side 146 of each tooth 128 can also define a secondary surface 151 positioned between the cutting face 150 and the trough 143 of the rotationally leading flute 126. The secondary surface 151 can have a concave, curved profile joining the flute trough 143 with the cutting face 150. The cutting face 150 can be referred to as a primary cutting face of the associated tooth 128 and the secondary surface 151 can be referred to as a secondary cutting face of the tooth 128.

Each tooth 128 can include a cutting tip 152 at the distal terminus of the tooth 128. The cutting tip 152 can be a single point, as shown, although other geometries, such as a distal edge, are within the scope of the present disclosure. The cutting tip 152 can define the distal-most point of the associated cutting face 150. In the present embodiment, the cutting tip 152 of each tooth 128 can be positioned radially outward with respect to the cutting tips 52 of the embodiment of FIGS. 1 through 18, as set forth in more detail below.

Figure 27:
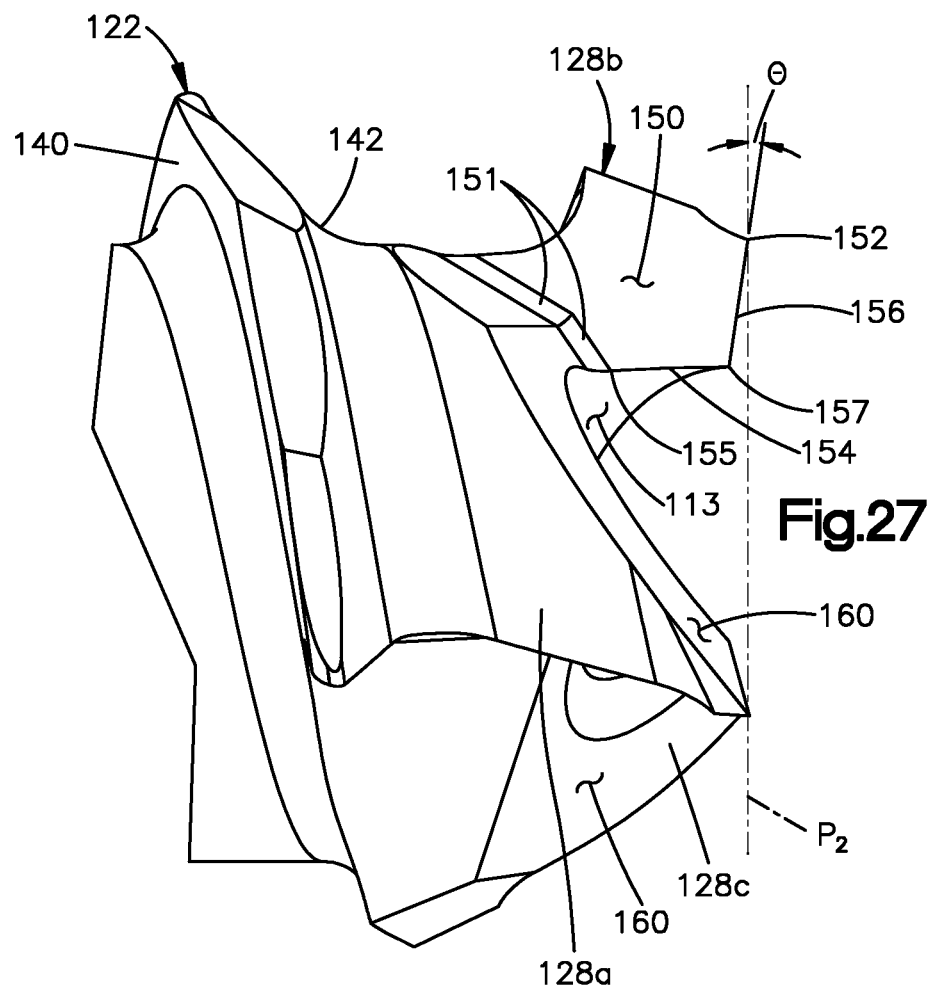
FIG. 27 is another side view of the distal end of the cannulated bone screw of FIG. 19.

FIG. 27 illustrates the distal end 108 of the bone screw 102 with the first tooth 128a generally oriented at the top of the figure. As shown with respect to the first tooth 128a, each tooth 128 can define a first cutting edge 154 located at an interface between the cutting face 150 and the interior surface 113 of the body 104. The first cutting edge 154 can define an edge proximal end 155 at an interface with the secondary surface 151 and an edge distal end 157 spaced distally from the edge proximal end 155. The first cutting edge 154 can be oriented or otherwise configured to slice or otherwise cleave bone material substantially similarly to the first cutting edge 54 of the embodiments set forth above with reference to FIGS. 1 through 18.

Each tooth 128 can also define a second cutting edge 156 extending radially outwardly and distally from a distal end 155 of the first cutting edge 154 to the cutting tip 152. The cutting tips 152 of the first, second, and third teeth 128a-c can collectively define a second plane $P_4$ that is orthogonal to the longitudinal axis X of the bone screw 102 (FIG. 24). Stated differently, the cutting tips 152 of each of the teeth 128 can be spaced from the proximal end 106 of the bone screw 102 at substantially the same distance along the longitudinal direction L and can each thus define the distal end 108 of the bone screw 102. Thus, by placing each of the cutting tips 152 against a surface (such as an outer surface of a target bone), the physician can gain a tactile indication of when the screw 102 is oriented substantially orthogonal to the surface. Because the cutting tips 152 of the present embodiment are located radially outwardly with respect to those of the embodiment of FIGS. 1 through 18, the present embodiment can provide an even greater tactile indication of when the screw 102 is oriented substantially orthogonal to the bone surface.

The second cutting edge 156 can be oriented so as to define an inward cutting edge angle θ of the associated tooth 128 with respect to the second plane $P_4$. The cutting edge angle θ can optionally be consistent from the rotationally leading side 146 to the rotationally trailing side 148 of the tooth 128; however, other geometries are within the scope of the present disclosure. The second cutting edge 156 can be oriented or otherwise configured to slice or otherwise cleave bone material substantially similarly to the second cutting edge 56 of the embodiments set forth above with reference to FIGS. 1 through 18. As the screw 102 is both rotated and advanced distally during insertion, each of the first and second cutting edges 154, 156 can slice or otherwise cleaves bone material along a helical path. At the cutting face 150, the second cutting edge 156 can define the rotationally leading edge of the relief surface 160. The relief surfaces 160 of the teeth 128 of the present embodiment can be substantially planar, and thus can be termed "straight" relief surfaces. The straight relief surfaces 160 of the present embodiment can be formed by milling or otherwise planarizing the helical relief surfaces 60 the embodiments of FIGS. 1 through 18, by way of non-limiting example. The straight relief surfaces 160 can provide the cutting teeth 128 of the present embodiment with a more angular profile, and reduce the cross-section of each tooth 128 as it slices through bone material. Other surfaces of the teeth 128 can also be milled or otherwise planarized to further reduce the cross-section of each tooth 128.

Referring again to FIG. 24, a non-limiting example of an orthogonal side view of the distal end 108 of the bone screw 102 is shown with the cutting tip 152 of the first tooth 128a directly overlying the longitudinal axis X. Thus, the longitudinal axis X of the screw 102 and the cutting tip 152 of the first tooth 128a can jointly define a longitudinal plane $P_3$ of the first tooth 128a. In FIG. 24, the longitudinal plane $P_3$ extends along the radial direction R directly into/out of the page. At this orientation, the cutting face 150 of the first tooth 128a can also extend along the radial direction R directly into/out of the page. The cutting face 150 of the first tooth 128a can be oriented at a first rake angle $\beta_1$ with respect to the longitudinal plane $P_3$ of the first tooth 128a. The first rake angles $\beta_1$ of the cutting faces 150 of the second and third teeth 128b, 128c can be defined in like manner. For example, the cutting face 150 of the second tooth 128b can be oriented at a first rake angle $\beta_1$ with respect to a longitudinal plane defined by the longitudinal axis X and the cutting tip 152 of the second tooth 128b. Similarly, the cutting face 150 of the third tooth 128c can be oriented at a first rake angle β with respect to a longitudinal plane defined by the longitudinal axis X and the cutting tip 152 of the first tooth 128c.

It is to be appreciated that the first rake angle $\beta_1$ and the flute offset angle α can be substantially equivalent. Thus, each cutting face 150 can have a first rake angle $\beta_1$ in the range of about 5 degrees and about 25 degrees with respect to the longitudinal axis X. In additional embodiments, the first rake angle $\beta_1$ can be in the range of about 10 degrees and about 20 degrees. In other embodiments, the first rake angle $\beta_1$ can be in the range of about 14 degrees and about 18 degrees. In further embodiments, the first rake angle $\beta_1$ can be about 16 degrees. In yet further embodiments, the first rake angle $\beta_1$ can be in the range of about 25 degrees and about 60 degrees or greater than 60 degrees. It is to be appreciated that, as described above, the first rake angle $\beta_1$ can be different (i.e., greater or less than) the flute offset angle α.

Additionally, similarly as described above with reference to FIG. 6B, the cutting face 150 of each tooth 128a-c of the present embodiment can also define a positive second rake angle $\beta_2$ with respect to a reference line intersecting the longitudinal axis X and the radially outermost edge of the cutting face 150 in a reference plane orthogonal to the longitudinal axis X.

Figure 28:
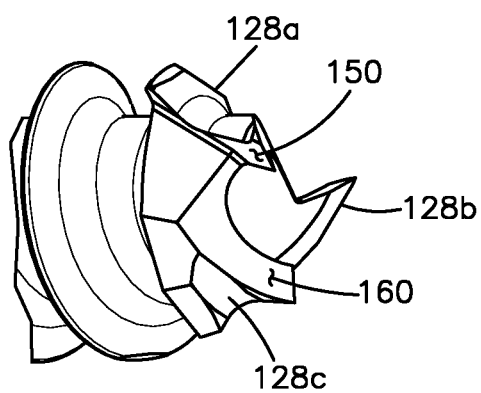
FIGS. 28 through 30 are additional perspective views of the distal end of the cannulated bone screw of FIG. 19.
Figure 29:
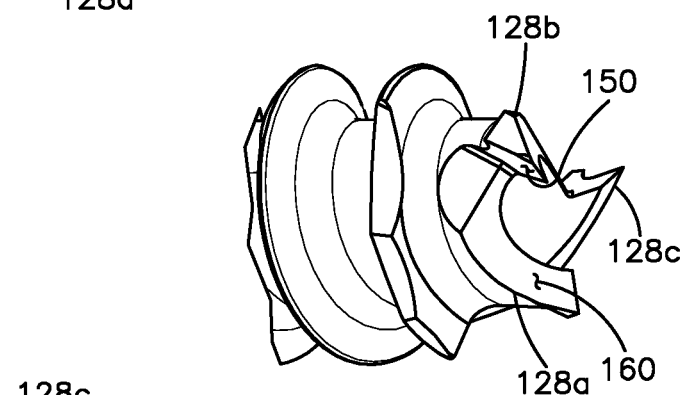
Figure 30:
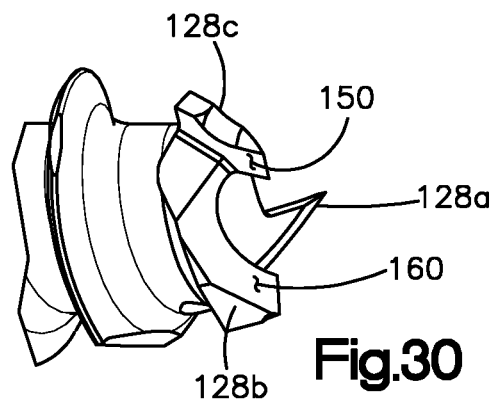

FIGS. 28 through 30 illustrate additional perspective views of the cutting teeth 128 at the distal end 108 of the bone screw 102. In FIG. 28, the first tooth 128a is oriented at the top of the view. In FIG. 29, the second tooth 128b is oriented at the top of the view. In FIG. 30, the third tooth 128c is oriented at the top of the view. As can be seen in FIGS. 25 through 30, each of the first, second, and third teeth 128a-c can define at least a portion of the shaft thread 122. As set forth above, the helix angle ψ can be uniform along the entire length of the threaded shaft region 120, including along the teeth 128.

Figure 32:
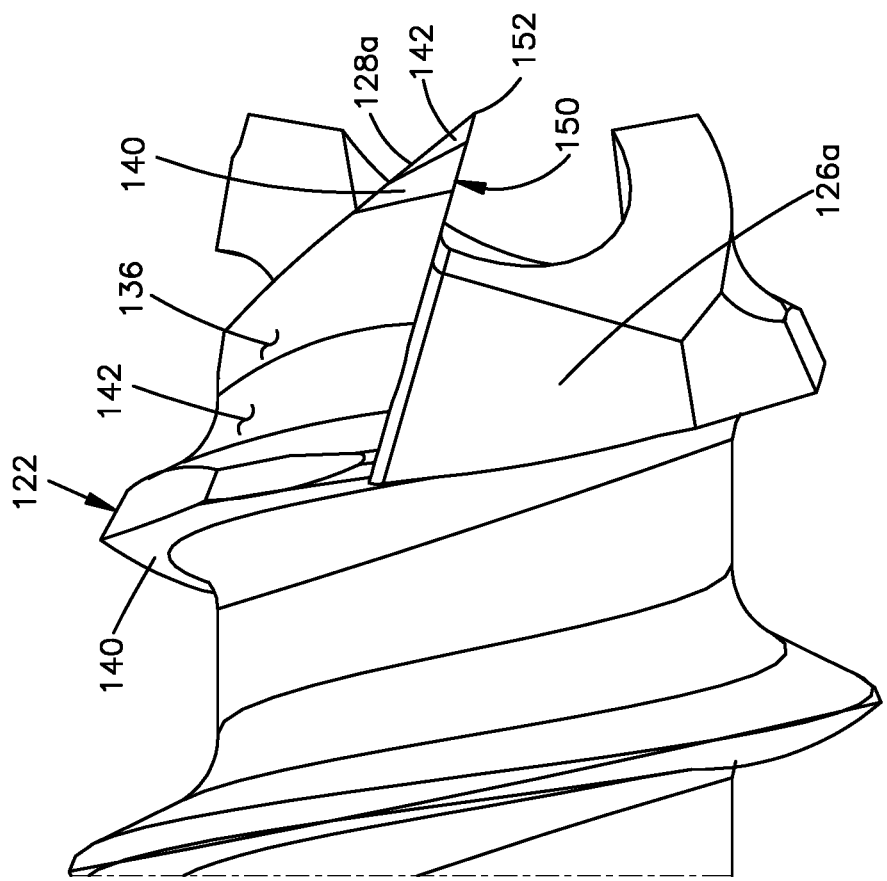
FIG. 32 is a side view of the distal end of the cannulated bone screw of FIG. 19 with the first cutting tooth rotated toward a center of the view.
Figure 31:
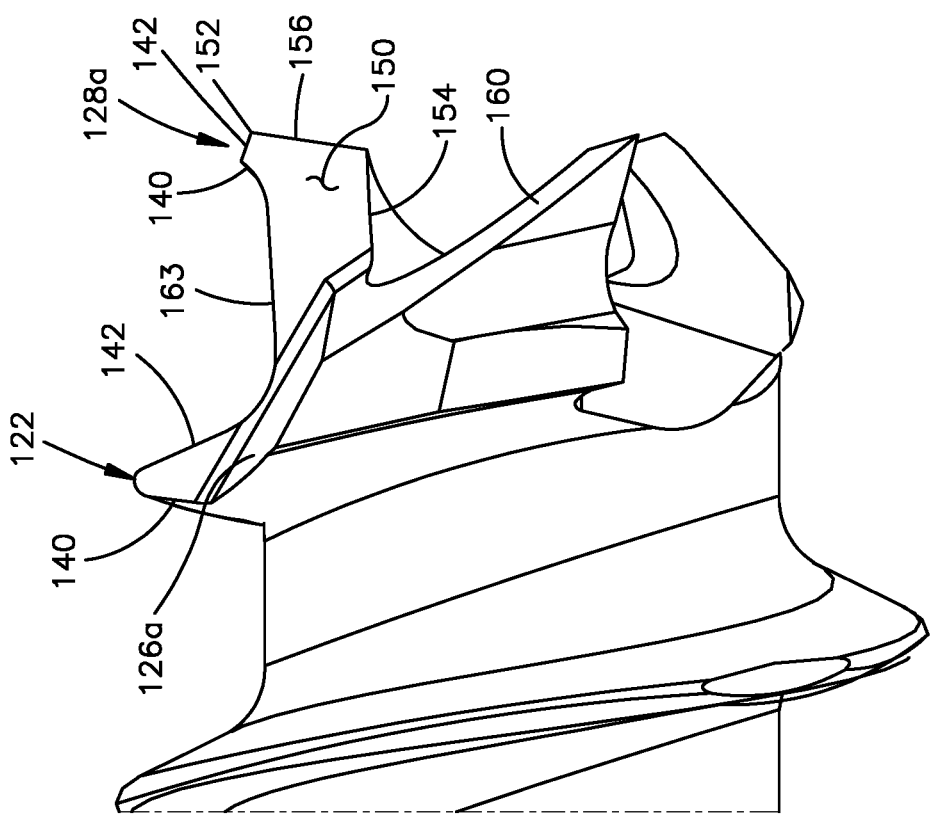
FIG. 31 is a side view of the distal end of the cannulated bone screw of FIG. 19 with a first cutting tooth positioned near the top of the view.
Figure 34:
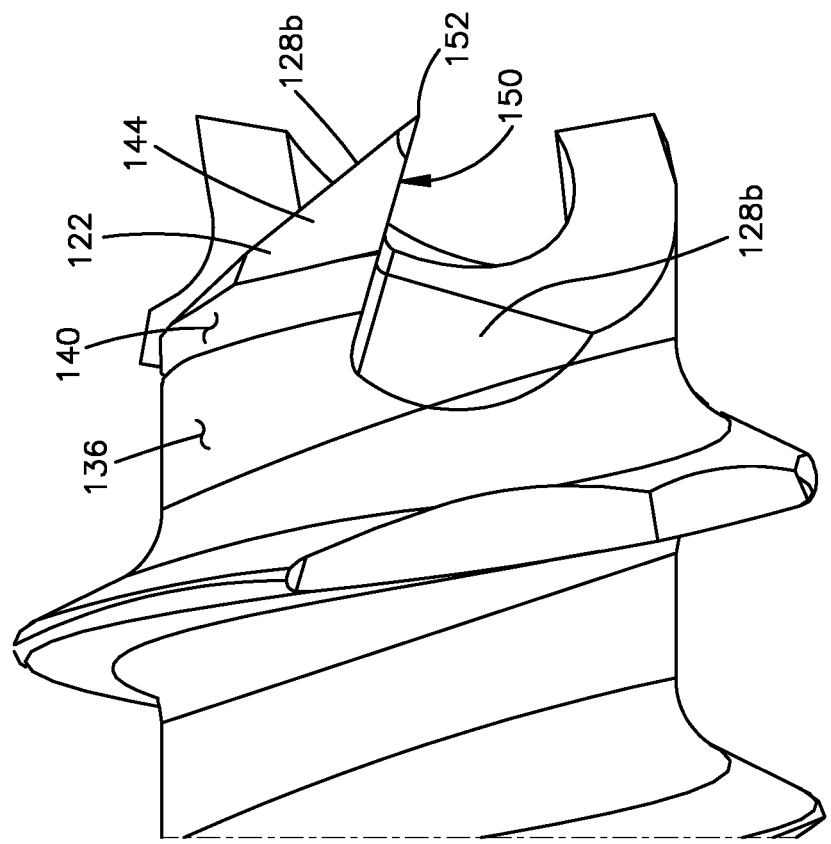
FIG. 34 is a side view of the distal end of the cannulated bone screw of FIG. 19 with the second cutting tooth rotated toward a center of the view.
Figure 33:
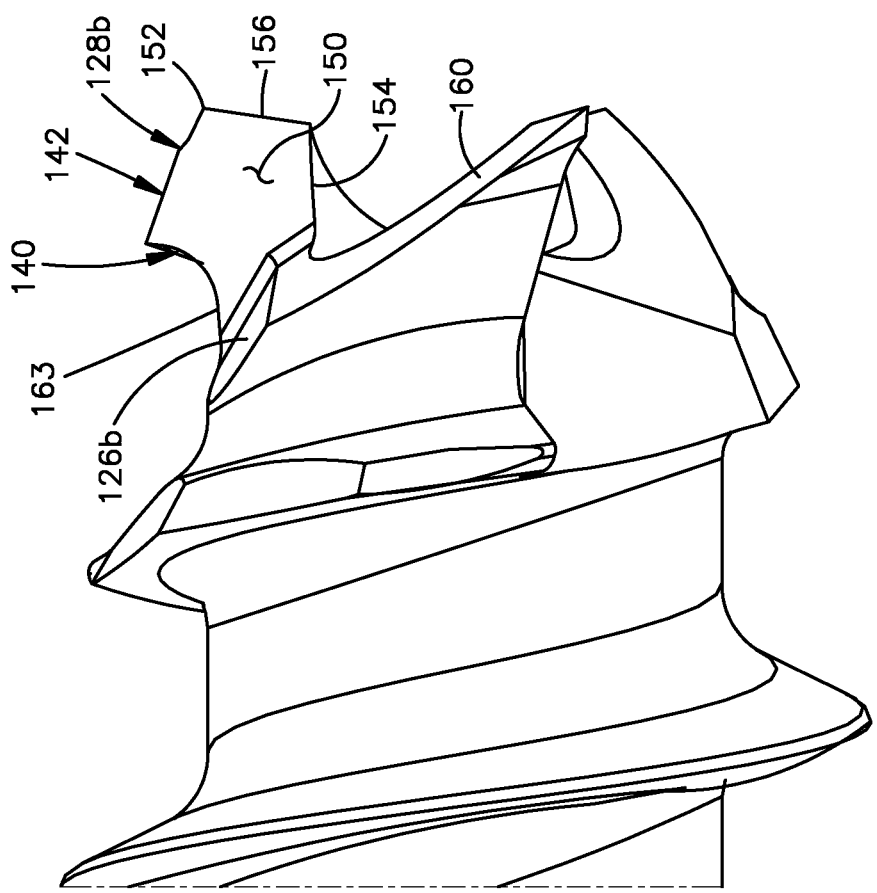
FIG. 33 is a side view of the distal end of the cannulated bone screw of FIG. 19 with a second cutting tooth positioned near the top of the view.
Figure 36:
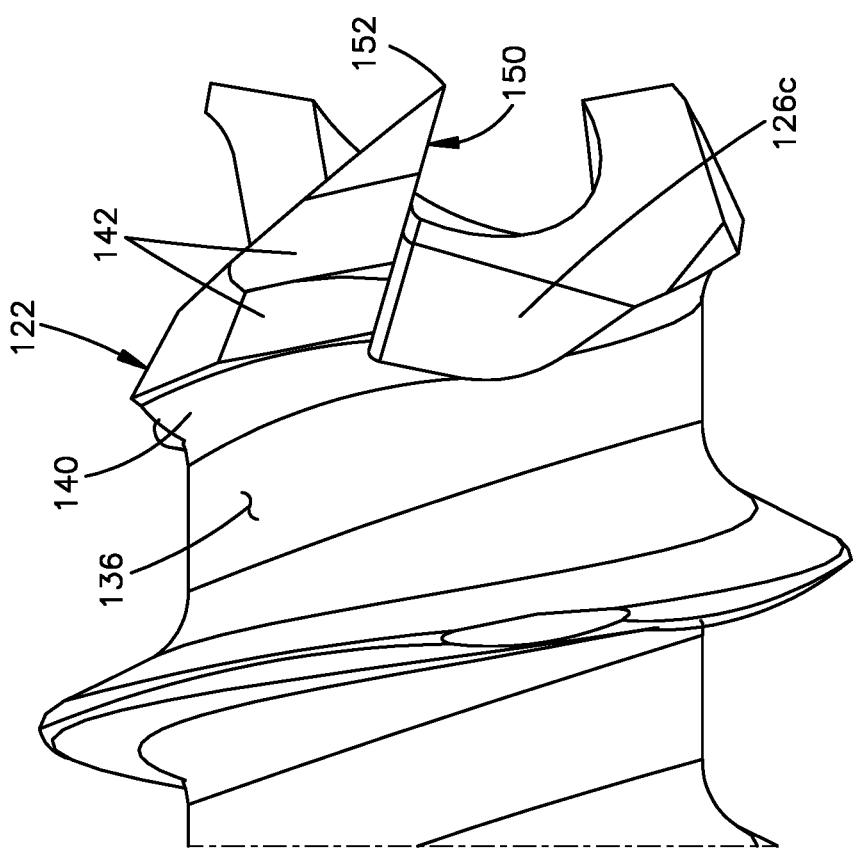
FIG. 36 is a side view of the distal end of the cannulated bone screw of FIG. 19 with the third cutting tooth rotated toward a center of the view.
Figure 35:
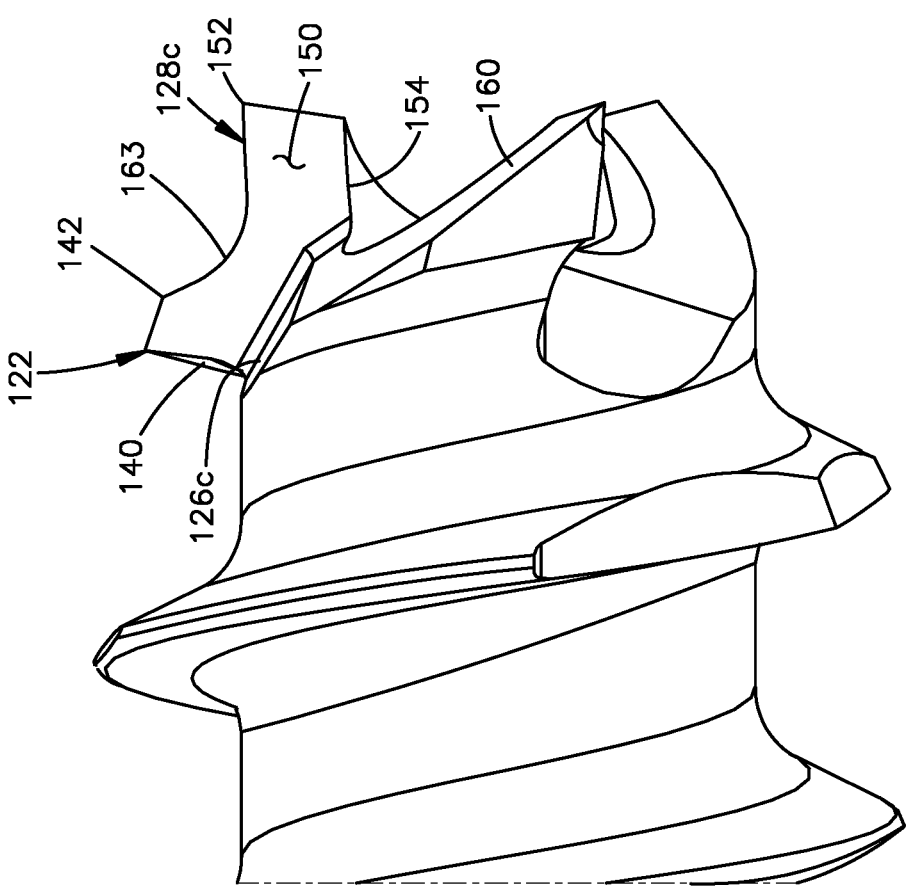
FIG. 35 is a side view of the distal end of the cannulated bone screw of FIG. 19 with a third cutting tooth positioned near the top of the view.

Referring now to FIGS. 31 through 36, the configuration and operation of the teeth 128 will be further discussed. FIGS. 31 and 32 illustrate the first tooth 128a as it rotates from the top of the view (FIG. 31) to a point where the cutting face 150 extends perpendicularly into the page (FIG. 32). FIGS. 33 and 34 illustrate the second tooth 128b as it rotates from the top of the view (FIG. 33) to a point where the cutting face 150 extends perpendicularly into the page (FIG. 34). FIGS. 35 and 36 illustrate the third tooth 128c as it rotates from the top of the view (FIG. 35) to a point where the cutting face 150 extends perpendicularly into the page (FIG. 36).

As shown in FIGS. 31 and 32, the first tooth 128a can define a portion of the shaft thread 122. In particular, a third cutting edge 163 of the cutting face 150 of the first tooth 128a can define an undercut 140 and front slope 142 thread portion. The third cutting edge 163 can also define another undercut 140 and front slope 142 thread portion adjacent the distal tip 152 of the tooth 128a. The third cutting edge 163 can provide the first tooth 128a with self-tapping functionality.

As shown in FIGS. 33 and 34, the second tooth 128b can also define a portion of the shaft thread 122. In particular, a third cutting edge 163 of the cutting face 150 of the second tooth 128b can define an undercut 140 and front slope 142 thread portion adjacent the distal tip 152 of the tooth 128b. The third cutting edge 163 can provide the second tooth 128b with self-tapping functionality.

As shown in FIGS. 35 and 36, the third tooth 128c can also define a portion of the shaft thread 122. In particular, a third cutting edge 163 of the cutting face 150 of the third tooth 128c can define an undercut 140 and front slope 142 thread portion between the proximal end distal ends of the third tooth 128c. The third cutting edge 163 can provide the third tooth 128c with self-tapping functionality.

Thus, the shaft thread 122 can essentially extend distally along the helical path 124 from the proximal end of the first tooth 128a to a position at least adjacent the cutting tip 152 of the third tooth 128c. The shaft thread 122 can intersect at least a portion of each of the cutting faces 150 of the teeth 128 so that the external thread 122 defines at least a portion of each cutting face 150. As the axial and rotational components $F_A$, $F_R$ of the drive force are applied and the bone screw 102 is driven into bone, the third cutting edge 163 of the first tooth 128a can form within the bone material a first helical channel through which at least a portion the shaft thread 122 can extend. Additionally, the third cutting edge 163 of the second tooth 128b can form within the bone material a second helical channel through which at least a portion of the shaft thread 122 can extend. Furthermore, the third cutting edge 163 of the third tooth 128c can form within the bone material a third helical channel through which at least a portion of the shaft thread 122 can extend. As the bone screw 102 makes a full revolution (i.e., 360 degrees about the longitudinal axis X) while being advanced distally into the bone material, the first, second, and third channels can merge into a substantially single helical channel through which the shaft thread 122 can extend as the screw 102 continued to advance.

It is to be appreciated that the cutting tip 152 and the rake angles $\beta_1$, $\beta_2$ of the cutting face 150 of each tooth 128 can allow each tooth 128 to promptly bite into (i.e., penetrate) and advance through cortical bone material responsive to the driving force without undue scraping or twisting of the screw 102 against the bone. Additionally, the first, second, and third cutting edges 154, 156, 163 can effectively separate bone material by a slicing separation mechanism that substantially does not include a scraping or shearing separation mechanism.

Referring now to FIG. 37, the inventor tested the cannulated bone screws 2, 102 disclosed herein within a block of 50 pcf foam, which can be analogous to bone material. A third cannulated bone screw 202 having straight cutting flutes (i.e., cutting flutes parallel with the longitudinal axis X) and straight relief surfaces was also tested in the foam block. While the inventor determined that the bone screws 2, 102 disclosed herein may not require significantly less insertion torque than the straight-flute screw 202, the inventor did discover that the bone screws 2, 102 disclosed herein require significantly fewer rotations than the straight-flute screw 202 to reach a particular depth within the foam block, as shown in the graph of FIG. 37.

Additionally, as shown in FIG. 38, a prior art screw similar to the screw 202 of FIG. 37 (having straight cutting flutes) was driven into a foam block 302 that approximates bone material. In particular, the foam block 302 included a top layer of 50 pcf foam 3 mm thick, which layer simulates cortical bone material. Underlying the top layer was a layer of 20 pcf foam, which simulates cancellous bone material. A layer of adhesive about 1 mm thick was disposed between the top and underlying foam layers. As can be seen, the prior art cannulated bone screw generates cutting particulates 303 that accrue on the engaged surface of the foam block 302 without any defined cutting chip structure. FIG. 39 illustrates a cannulated bone screw with angled cutting flutes, similar to the bone screws 2, 102 disclosed herein, being driven into the foam block 302. While the screw with angled flutes also generates some cutting particulates, it also produces a single, helical chip strand or filament 310 that is conveyed away from the engaged foam material.

Moreover, the cannulated bone screws 2, 102 disclosed herein have been observed to provide the user with favorable tactile feedback, as set forth above. For example, the bone screws 2, 102 have been observed to bite into cortical bone material substantially immediately responsive to a rotational drive force $F_R$. Additionally, the tactile feedback provided by the screws 2, 102 can allow the physician to vary the axial and rotational components $F_A$, $F_R$ of the driving force so that the threaded portion 20 of the shaft can be inserted within bone substantially without generating any cutting particles. For example, FIG. 40 illustrates an image from a test where nearly the entire shaft thread 22, 122 of the bone screw 2, 102 was able to be inserted within a foam block 304 substantially without generating any cuttings.

It is to be appreciated that the foregoing dimensions of the cannulated bone screws 2, 102 disclosed herein represent non-limiting examples of the sizes, shapes, and orientations of the bone screws 2, 102 and their components. Furthermore, the bone screws 2, 102 can be scaled to sizes that are larger or smaller than those disclosed herein without departing from the scope of the embodiments of the present disclosure.

Although the cutting flutes 26, 126 (and the respective cutting faces 50, 51, 150, 151 defined thereby) of the shaft thread 22, 122 and the cutting flutes 37, 137 of the shaft thread 32, 132 are depicted each extending along a linear path, it is to be appreciated the cutting flutes 26, 126, 37, 137 can optionally extend along a helical path. In such embodiments, the flute angles $\alpha$, $\alpha_2$ and first rake angles $\beta_1$ can be characterized as helix angles. Moreover, although the primary cutting faces 50, 150 of the teeth 28, 128 are shown as having a linear profile in a reference plane orthogonal to the longitudinal axis X, the primary cutting faces 50, 150 can optionally have a concave profile in the reference plane orthogonal to the longitudinal axis X.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed is:

1. A bone screw, comprising:
a proximal end and a distal end spaced from the proximal end in a distal direction along a longitudinal axis of the bone screw;
a cannulation extending from the proximal end to the distal end;
a threaded region extending along at least a portion of a length of the screw, the length extending from the proximal end to the distal end, the threaded region defining at least one external thread that extends about the longitudinal axis along a helical path, the threaded region including at least one flute that extends to the distal end of the bone screw, the at least one flute defining at least one cutting tooth that, in turn, defines a cutting face on a rotationally leading side of the at least one cutting tooth, wherein each cutting face is oriented so as to define an angle with respect to the longitudinal axis, the angle in the range of 5 degrees to 25 degrees,
wherein the at least one flute circumferentially interrupts at least a portion of the at least one external thread, and
wherein each cutting face defines a cutting edge that extends away from an interface with the cannulation both distally and radially outwardly to a cutting tip at a distal terminus of the at least one cutting tooth.

2. The bone screw of claim 1, wherein at least a portion of each cutting face intersects the at least one external thread so that the at least one external thread defines at least a portion of the respective cutting face.

3. The bone screw of claim 1, wherein the at least one external thread extends from the cutting face on a rotationally trailing side of the at least one cutting tooth circumferentially opposite the leading side of the tooth.

4. The bone screw of claim 1, wherein the angle is in the range of 10 degrees to 20 degrees.

5. The bone screw of claim 4, wherein the angle is in the range of 14 degrees to 18 degrees.

6. The bone screw of claim 5, wherein the angle is 16 degrees.

7. The bone screw of claim 1, further comprising a head at the proximal end of the bone screw, wherein the head defines a second threaded region defining an external thread.

8. The bone screw of claim 7, wherein the external thread of the second threaded region includes at least one second flute defining a second central flute axis that is offset from the longitudinal axis by an angle in the range of 5 degrees to 25 degrees.

9. A bone screw, comprising:
a proximal end and a distal end spaced from the proximal end in a distal direction along a longitudinal axis of the bone screw;
a cannulation extending from the proximal end to the distal end;
a threaded region extending along at least a portion of a length of the screw, the length extending from the proximal end to the distal end, the threaded region defining at least one external thread that extends about the longitudinal axis along a helical path, the threaded region including a plurality of cutting flutes spaced circumferentially with respect to one another, each of the plurality of cutting flutes extending to the distal end of the bone screw, the plurality of cutting flutes defining a plurality of teeth spaced circumferentially between the cutting flutes of the plurality of cutting flutes, each of the plurality of teeth defining a cutting face on a rotationally leading side of the respective tooth, wherein each cutting face is oriented so as to define an angle with respect to the longitudinal axis, the angle in the range of 5 degrees to 25 degrees,
wherein each of the plurality of cutting flutes circumferentially interrupts at least a portion of the at least one external thread, and
wherein each cutting face defines a cutting edge that extends away from a respective interface with the cannulation both distally and radially outwardly to a cutting tip at a distal terminus of the respective tooth.

10. The bone screw of claim 9, wherein the helical path defines a helix.

11. The bone screw of claim 9, wherein the cutting face of each of the plurality of teeth defines the cutting tip of the associated tooth.

12. The bone screw of claim 11, wherein the distal termini of each of the plurality of teeth are located on a single plane that is oriented normal to the longitudinal axis.

13. The bone screw of claim 9, wherein at least a portion of each of the plurality of cutting flutes intersects the cannulation.

14. The bone screw of claim 9, wherein each of the plurality of teeth defines a relief surface extending circumferentially between the rotationally leading side of the respective tooth and a rotationally trailing side of the respective tooth.

15. The bone screw of claim 14, wherein each relief surface is substantially helical.

16. The bone screw of claim 14, wherein at least a portion of each relief surface is substantially planar.

17. The bone screw of claim 9, wherein the cutting face of each of the plurality of teeth is substantially planar.

18. The bone screw of claim 9, wherein an additional cutting edge of the cutting face defines at least a portion of the at least one external thread.

19. The bone screw of claim 18, wherein:
the plurality of cutting flutes consist of three cutting flutes, and
the plurality of teeth consist of three teeth.

* * * * *